(12) United States Patent
Tamura et al.

(10) Patent No.: US 8,920,164 B2
(45) Date of Patent: Dec. 30, 2014

(54) ORTHODONTIC DEVICE AND METHOD FOR MOUNTING AND REMOVING ORTHODONTIC CAP

(75) Inventors: Hajime Tamura, Tokyo (JP); Kiyoshi Shiga, Fukushima (JP)

(73) Assignee: Tomy Incorporated, Fukushima (JP)

( * ) Notice: Subject to any disclaimer, the term of this patent is extended or adjusted under 35 U.S.C. 154(b) by 0 days.

(21) Appl. No.: 13/320,563

(22) PCT Filed: May 15, 2009

(86) PCT No.: PCT/JP2009/059095
§ 371 (c)(1),
(2), (4) Date: Nov. 15, 2011

(87) PCT Pub. No.: WO2010/131368
PCT Pub. Date: Nov. 18, 2010

(65) Prior Publication Data
US 2012/0058443 A1  Mar. 8, 2012

(51) Int. Cl.
*A61C 3/00* (2006.01)
*A61C 7/28* (2006.01)

(52) U.S. Cl.
CPC ..................................... *A61C 7/287* (2013.01)
USPC ............................................................ 433/10

(58) Field of Classification Search
USPC ...................................................... 433/8–17
See application file for complete search history.

(56) References Cited

U.S. PATENT DOCUMENTS

| | | | | |
|---|---|---|---|---|
| 3,391,461 A | * | 7/1968 | Johnson | 433/17 |
| 4,355,975 A | * | 10/1982 | Fujita | 433/11 |
| 4,551,094 A | * | 11/1985 | Kesling | 433/8 |
| 5,269,681 A | * | 12/1993 | Degnan | 433/11 |
| 6,733,286 B2 | * | 5/2004 | Abels et al. | 433/11 |
| 2002/0110777 A1 | * | 8/2002 | Abels et al. | 433/11 |
| 2004/0209219 A1 | * | 10/2004 | Miyaji et al. | 433/10 |
| 2004/0259048 A1 | * | 12/2004 | Balabanovsky | 433/10 |
| 2005/0266369 A1 | * | 12/2005 | Scommegna et al. | 433/15 |
| 2006/0172248 A1 | * | 8/2006 | Sernetz et al. | 433/8 |
| 2010/0129765 A1 | * | 5/2010 | Mohr et al. | 433/10 |

FOREIGN PATENT DOCUMENTS

| | | |
|---|---|---|
| CN | 1494402 A | 5/2004 |
| CN | 101014298 A | 8/2007 |
| JP | 3146052 A | 6/1991 |
| JP | 3168142 A | 7/1991 |

(Continued)

OTHER PUBLICATIONS

International Search Report dated Jun. 16, 2009 from the International Searching Authority in counterpart application No. PCT/JP2009/059095

(Continued)

*Primary Examiner* — Heidi M Eide
(74) *Attorney, Agent, or Firm* — Sughrue Mion, PLLC

(57) ABSTRACT

An orthodontic device (10) according to the invention having an orthodontic attachment (11) which includes an engaging portion (17) formed in a side portion of an archwire slot (16), and an orthodontic cap (13) mounted on the orthodontic attachment (11) while covering the whole of the archwire slot (16) and includes an engaging/receiving portion (22) extending in a direction perpendicular to a mesiodistal direction of the archwire (12) and engageable with the engaging portion (17). A method for mounting and removing an orthodontic cap which to facilitate the mounting and removing of the orthodontic cap with respect to the orthodontic attachment.

12 Claims, 27 Drawing Sheets

(56) References Cited

FOREIGN PATENT DOCUMENTS

| JP | 687861 B2 | 11/1994 |
| JP | 10337294 A | 12/1998 |
| JP | 2867498 B2 | 3/1999 |
| JP | 2867499 B2 | 3/1999 |
| JP | 2004329912 A | 11/2004 |
| JP | 2008511359 A | 4/2008 |
| JP | 3149245 U | 3/2009 |
| WO | 02/065939 A1 | 8/2002 |

OTHER PUBLICATIONS

Written Opinion of the International Searching Authority dated Jun. 16, 2009 in counterpart international application No. PCT/JP2009/059095.

Communication dated May 7, 2013 from the Japanese Patent Office in counterpart application No. 2011-513202.

Office Action, dated for Dec. 30, 2013, issued by the State Intellectual Property Office of the People's Republic of China in counterpart Chinese Application No. 200980159316.2.

* cited by examiner

ORTHODONTIC DEVICE AND METHOD FOR MOUNTING AND REMOVING ORTHODONTIC CAP

TECHNICAL FIELD

The present invention relates to an orthodontic device including an orthodontic attachment with an archwire retained thereon for correcting a teeth row using the archwire, and an orthodontic cap to be mounted onto the orthodontic attachment, and a method for mounting and removing the orthodontic cap.

BACKGROUND ART

Conventionally, an orthodontic treatment is carried out by retaining an archwire on an attachment such as a bracket or a tube mounted on teeth and transmitting the restoring force of the archwire to the teeth. Therefore, in order to retain the archwire within an archwire slot formed in the bracket, generally, there is used, for example, an elastomeric ring made of synthetic resin such as urethane resin or silicone resin, or a connecting wire such as a ligature wire made of metal, which can be caught on tie wings of the bracket for retaining the archwire.

However, the elastomeric ring, due to the property of its material, under the intraoral environment, deteriorates and loses its elasticity or is easy to break, so that it must be replaced frequently. Consequently, it has become a large burden to a patient and a doctor.

On the other hand, in the case of the ligature wire, since it is made of metal, the degree of ligation is hard to decide. That is, when it is ligated too tight, frictional resistance between the archwire and archwire slot increases to fail to obtain a desired correcting force, which causes the extended treatment period. Further, there is a fear that the cut end of the wire can damage the oral mucosa of a patient.

Thus, in order to solve the above problems, there has been demanded a ligating tool which can be easily mounted onto and removed from a bracket, can reduce its frictional resistance with respect to an archwire and can provide an aesthetic appearance.

In view of the above circumstances, there is proposed a ligating sheet made of elastic material which can cover the entire surface of the bracket and ligate the archwire to thereby reduce its frictional resistance with respect to the archwire and thus move the teeth smoothly (see, for example, the patent reference 1).

There is also known an orthodontic bracket cap (for example, see the patent reference 2, 3 and 4) made of elastic material having a color approximate to the teeth color which, similarly to the above reference 1, while covering the entire surface of the bracket, ligates the archwire and also includes a hook for mounting an auxiliary wire and a fitting portion to be fitted with the bracket.

On the other hand, there is further known a cross-shaped ligating tool which can be used while it is engaged between the archwire slot and mesiodistal tie wings (for example, see the patent reference 5).

PRIOR ART TECHNOLOGY REFERENCE

Patent Reference

Patent Reference 1: Japanese Patent Publication Hei-6-87861-B

Patent Reference 2: Japanese Patent Publication Hei-3-146052-A

Patent Reference 3: Japanese Patent No. 2867498-B

Patent Reference 4: Japanese Patent No. 2867499-B

Patent Reference 5: Japanese Patent Publication 2004-329912-A

DISCLOSURE OF THE INVENTION

Problems that the Invention is to Solve

However, in the conventional orthodontic device respectively disclosed in the above patent reference 1, 2, 3 and 4, the orthodontic bracket cap is hard to mount onto the attachment such as the bracket. Also, in order to cover the entire surface of the attachment, the ligating tool becomes large in size and gives a patient a strong strange feeling within the oral cavity.

Also, in the conventional orthodontic device disclose in the above patent referent 5, due to lack of versatility, multiple ligating tools different in size must be used in the respective portions of the attachment, which takes time and labor for a doctor to distinguish them and causes a patient to pay an increased doctor's fee.

Further, since such ligating tool is structured such that, when removing it from the attachment, it must be cut using a cutter or the like. This requires a troublesome operation.

The present invention aims at solving the above problems. Thus, it is an object of the invention to provide an orthodontic device and a method for mounting and removing an orthodontic cap in which, when retaining an archwire in an archwire slot formed in an orthodontic attachment, the archwire is retained with an orthodontic cap through the orthodontic attachment to thereby be able to reduce frictional resistance between the archwire and archwire slot.

Also, it is another object of the invention to provide an orthodontic device and a method for mounting and removing an orthodontic cap in which an orthodontic attachment and an archwire are covered with an orthodontic cap to thereby be able to provide an aesthetic appearance, and mounting and removing of the orthodontic cap with respect to the orthodontic attachment can be facilitated.

Means for Solving the Problems

The object of the invention can be achieved by an orthodontic device comprising:

an orthodontic attachment having an archwire slot which store an archwire therein; and, an orthodontic cap to be mounted on the orthodontic attachment, wherein the orthodontic attachment includes an engaging portion formed in a side portion of the archwire slot, and the orthodontic cap is mounted on the orthodontic attachment while covering the whole of the archwire slot and includes an engaging portion receiving portion extending in a direction perpendicular to an axial direction of the archwire and engageable with the engaging portion.

In the above-structured orthodontic device, when mounting the orthodontic cap onto the orthodontic attachment, the orthodontic attachment is bonded to teeth and the archwire is dropped down into the archwire slot of the orthodontic attachment. Next, the orthodontic cap is put onto the orthodontic attachment and the engaging portion receiving portion of the orthodontic cap is engaged with the engaging portion of the orthodontic attachment. In this case, the engaging portion receiving portion of the orthodontic cap is engaged with the engaging portion of the orthodontic attachment formed in a direction to perpendicular to the mesiodistal direction (axial direction) of the archwire.

Thus, the engaging portion receiving portion of the orthodontic cap can be easily engaged with the engaging portion of the orthodontic attachment formed at a position free from the influence of the archwire. Therefore, when the archwire is retained in the archwire slot, the orthodontic device can provide an aesthetic appearance and the orthodontic cap can be mounted easily.

In the above-structured orthodontic device, since the archwire dropped down into the archwire slot of the orthodontic attachment is retained by the orthodontic cap through the orthodontic attachment, the archwire can be retained without applying a load thereto directly. Therefore, when the archwire is retained in the archwire slot, frictional resistance between the archwire and archwire slot can be reduced.

The object of the invention can be achieved by the orthodontic device in which the engaging portion of the orthodontic attachment includes a cut-out portion for removing its engagement and, by inserting a removing device into the cut-out portion, the engaging portion receiving portion of the orthodontic cap is moved outwardly of the orthodontic attachment and is thereby removed from the engaging portion.

In the above-structured orthodontic device, when removing the engagement of the orthodontic device, by inserting a removing device such as tweezers into the cut-out portion of the orthodontic attachment to press against the engaging portion receiving portion, the engaging portion receiving portion of the orthodontic cap can be removed from the engaging portion of the orthodontic attachment, that is, the orthodontic cap can be removed from the teeth row connecting attachment. Therefore, removal of the engagement of the orthodontic device can be carried out simply.

In the above structure, it is preferable that the orthodontic cap includes an archwire support projection extending in a mesiodistal direction of the archwire slot and projecting into the archwire slot.

Thus, the archwire dropped down into the archwire slot, as the need arises, can be supported within the archwire slot by the archwire support projection of the orthodontic cap without looseness.

Further, in the above structure, it is preferable that the orthodontic cap includes a pair of cut-out recess portions respectively formed in two end portions thereof in the mesiodistal direction.

Thus, since, when the front teeth portion is twisted or when mounting the orthodontic cap onto the orthodontic attachment put on the lingual surfaces of the teeth, the orthodontic cap can be prevented from applying an excessive load to the archwire, friction resistance between the archwire and archwire slot can be reduced.

Further, in the above structure, it is preferable that the orthodontic cap includes a sub slot allowing insertion of an auxiliary wire therein.

Thus, the teeth can be pressed down or pulled up using the auxiliary wire inserted into the sub slot.

Further, in the above structure, it is preferable that the orthodontic cap includes a power arm.

Thus, by catching a chain, an elastic member, a coil spring or the like on the power arm, the mesiodistal movement of a canine or a premolar can be carried out.

Further, in the above structure, it is preferable that the orthodontic cap includes a hook.

Thus, by catching a chain, an elastic member, a coil spring or the like on the hook, the mesiodistal movement of a canine or a premolar can be carried out.

Further, in the above structure, it is preferable that the orthodontic cap has axial symmetry with respect to its mesiodistal direction and a tooth axial direction perpendicular to the mesiodistal direction.

Thus, since the orthodontic cap is formed to have axial symmetry with respect to its mesiodistal direction and a tooth axial direction perpendicular to the mesiodistal direction, that is, since the cap is free from the restrictions of the vertical direction and right and left direction, its mounting operation can be facilitated and also the engaging portion receiving portion of the orthodontic cap can be stably engaged with the engaging portion of the orthodontic attachment.

Further, in the above structure, it is preferable that it further includes a tab detachably connected to the orthodontic cap.

Thus, when mounting the orthodontic cap onto the orthodontic attachment after the orthodontic attachment is bonded to the teeth, by holding the tab, the handling of the orthodontic cap can be facilitated further.

Further, the object of the invention can be achieved by a method for mounting and removing an orthodontic cap to be mounted on an orthodontic attachment with an archwire slot which stores an archwire therein, wherein, when mounting the orthodontic cap, the orthodontic cap is put on the orthodontic attachment from above to thereby engage an engaging portion receiving portion formed in the orthodontic cap with an engaging portion formed in the archwire slot, and wherein when removing the orthodontic cap, by inserting a removing device into a cut-out portion for removing the engagement formed in the engaging portion, the engaging portion receiving portion of the orthodontic cap is moved outwardly of the orthodontic attachment and is thereby removed from the engaging portion.

In the above orthodontic cap mounting and removing method, when mounting the orthodontic cap, the engaging portion receiving portion thereof can be easily engaged with the engaging portion of the orthodontic attachment formed at a position free from the influence of the archwire. Also, when removing the cap, by inserting the removing device into the cut-out portion of the engaging portion, the engaging portion receiving portion can be easily removed from the engaging portion. Therefore, since the orthodontic attachment and archwire are covered with the orthodontic cap, there can be provided an aesthetic appearance and the orthodontic cap can be easily mounted onto and removed from the orthodontic attachment.

Also, since the archwire dropped down into the archwire slot of the orthodontic attachment is retained by the orthodontic cap through the orthodontic attachment, the archwire can be retained without applying any load thereto directly. This can reduce frictional resistance between the archwire and archwire slot.

Effective of the Invention

According to an orthodontic device and a method for mounting and removing an orthodontic cap of the invention, when retaining an archwire in an archwire slot formed in an orthodontic attachment, the archwire is retained with an orthodontic cap through the orthodontic attachment to thereby be able to reduce frictional resistance between the archwire and archwire slot.

Further, since an orthodontic attachment and an archwire are covered with an orthodontic cap, an aesthetic appearance can be provided, and mounting and removing of the orthodontic cap with respect to the orthodontic attachment can be facilitated.

MODE FOR CARRYING OUT THE INVENTION

Now, description will be given below of an orthodontic device and a method for mounting and removing an orthodontic cap according to multiple embodiments of the invention with reference to the accompanying drawings.

First Embodiment

Figure 1:
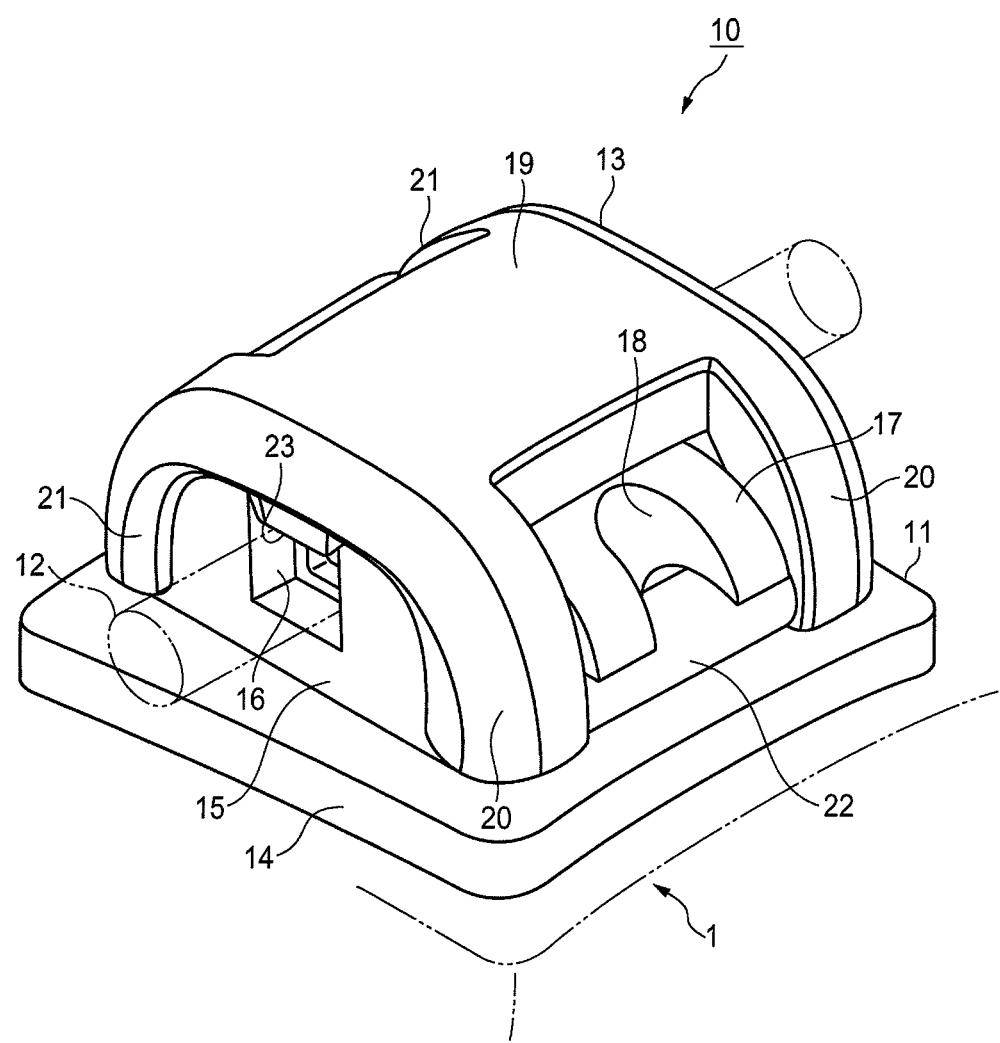
FIG. 1 It is a perspective appearance view of an orthodontic device according to a first embodiment of the invention, when viewed from obliquely upward.

As shown in FIG. 1, an orthodontic device 10 includes an orthodontic attachment 11 to be fixed to a tooth 1, an archwire 12 to be retained on the orthodontic attachment 11 and situated parallel to a row of teeth, and an orthodontic cap 13 to be mounted onto the orthodontic attachment 11.

Figure 2:
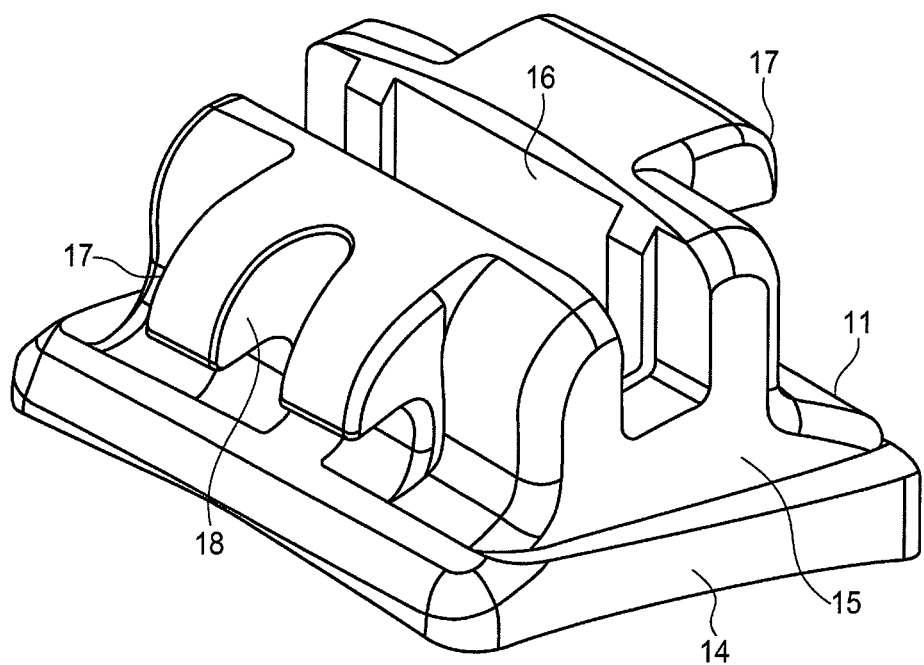
FIG. 2 It is a perspective appearance view of an orthodontic attachment to be applied to the orthodontic device shown in FIG. 1, when viewed from obliquely upward.
Figure 3:
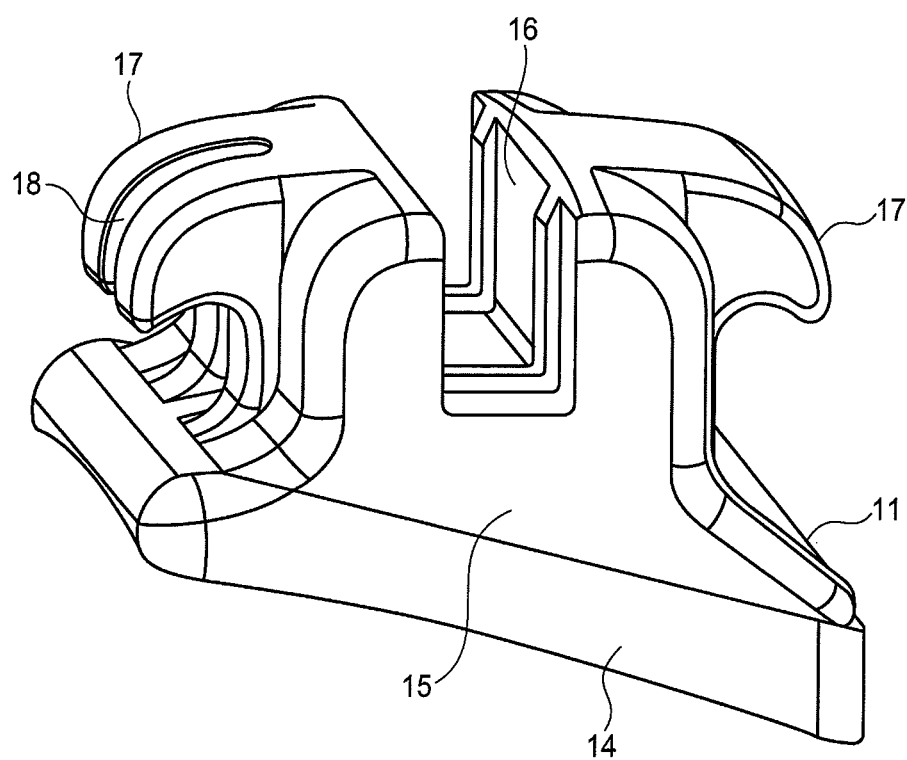
FIG. 3 It is a perspective appearance view of the orthodontic attachment shown in FIG. 2, when it is viewed with its archwire slot being situated in the front thereof.

As shown in FIGS. 2 and 3, the orthodontic attachment 11 includes a base 14 to be fixed to the surface of the tooth 1 with adhesive, an attachment main body 15 disposed on the base 14 and an archwire slot 16 formed in the attachment main body 15. The archwire slot 16 opens toward the two side portions of the attachment main body 15 and is formed in an angular groove shape having a dimension slightly larger than the outside diameter dimension of the metal-made archwire 12.

The orthodontic attachment 11 also includes a pair of engaging portions 17 respectively provided on and projected from the side portions of the archwire slot 16 of the attachment main body 15. Each engaging portion 17 is formed in a hook shape the leading end portion of which faces obliquely downward.

The orthodontic attachment 11 further includes a cut-out portion 18 formed in the central portion of the engaging portion 17 for removing the engagement thereof.

Figure 4:
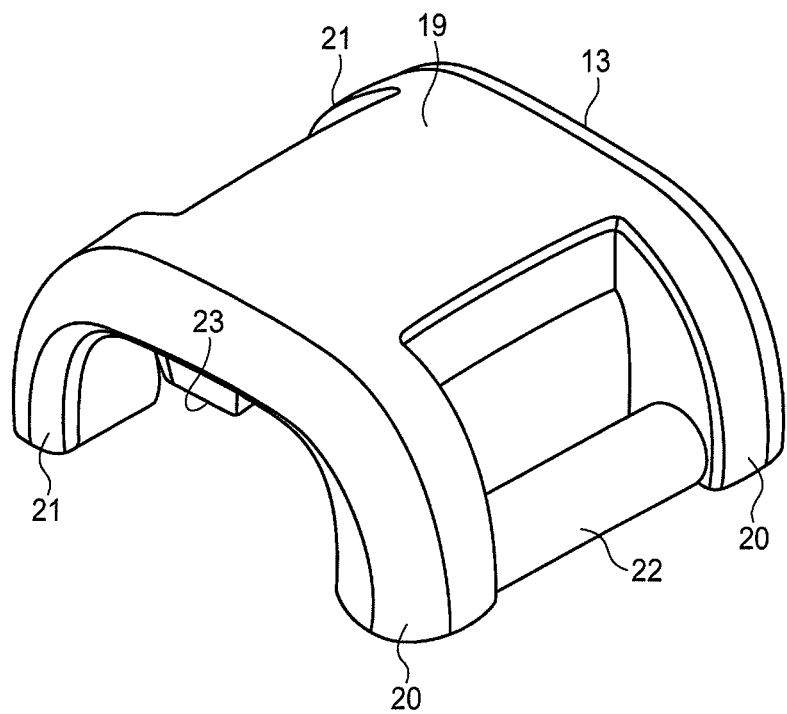
FIG. 4 It is a perspective appearance view of an orthodontic cap to be applied to the orthodontic device shown in FIG. 1, when viewed from obliquely upward.
Figure 5:
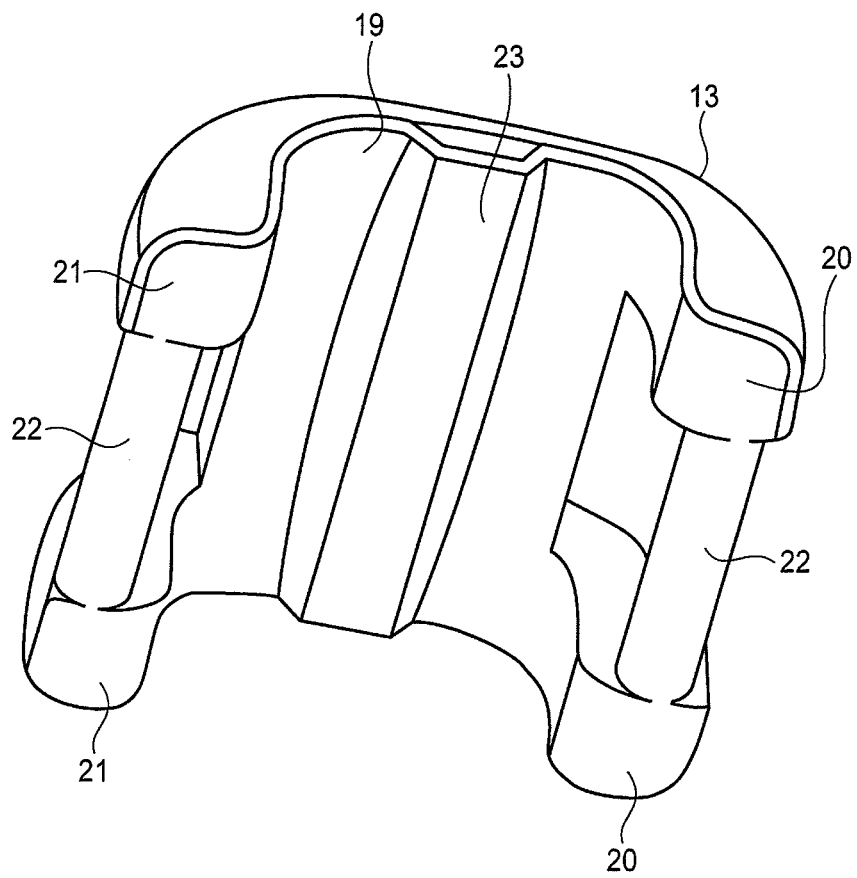
FIG. 5 It is a bottom view of the orthodontic cap shown in FIG. 4.

As shown in FIGS. 4 and 5, the orthodontic cap 13 includes a cap main body 19 disposed in the top portion thereof, and foot portions 20, 21 respectively formed two per each of the upper and lower portions of the cap main body 19. The orthodontic cap 13 also includes two engaging portion receiving portions 22 one of which is interposed between the pair of foot portions 20 disposed upwardly in a direction perpendicular to the mesiodistal direction of the archwire slot 16 of the orthodontic attachment 11, the other being interposed between the pair of foot portions 21 disposed downwardly in the direction perpendicular to the mesiodistal direction of the archwire slot 16. The engaging portion receiving portions 22 are respectively formed to have a cylindrical shape and are respectively engaged with their associated engagement portions 17 of the orthodontic attachment 11.

The orthodontic cap 13 is formed to have axial symmetry with respect to the mesiodistal direction and teeth axial direction perpendicular to the mesiodistal direction.

The orthodontic cap 13 includes an archwire support projection 23 which is provided on the bottom surface of the cap main body 19 to project therefrom in the mesiodistal direction of the archwire slot 16 of the orthodontic attachment 11 and can be inserted into the archwire slot 16. The archwire support projection 23 is not used to press against the archwire 12 inserted into the archwire slot 16 but has such a degree of function as to support the archwire 12 not to be too loose within the archwire slot 16.

The orthodontic attachment 11 includes an attachment to be mounted onto the labial surface of a tooth and an attachment to be mounted onto the lingual (back surface) side thereof (which is called a lingual bracket). That is, the orthodontic attachment 11 can be used in either portion.

As the material of the orthodontic attachment 11, there may preferably be used any one of metal, ceramics and plastics. More preferably, there may be used material such as ceramics or plastics which is easy to form and has an aesthetic property.

As the material of the orthodontic cap 13, preferably, there may be used thermoplastic resin or thermoplastic elastomer or a material constituted of a mixture of these materials, or thermosetting resin or thermosetting elastomer or a material constituted of a mixture of these materials.

The thermoplastic resin can include, for example, polypropylene, polyethylene, polycarbonate, polyacetal, and cycloolefin polymer.

The thermoplastic elastomer can include, for example, polyolefin elastomer, ethylene elastomer, polyamide elastomer, styrene elastomer, urethane elastomer, silicone elastomer, ethylene-vinyl acetate copolymer, and styrene-butadiene copolymer.

The thermosetting resin can include, for example, fluorine resin, phenolic resin, epoxy resin, urea resin, polyester resin, and melamine resin.

The thermosetting elastomer can include, for example, urethane elastomer and silicone elastomer.

In the orthodontic device 10, the base 14 of the orthodontic attachment 11 with the archwire slot 16 extending parallel to the teeth row is bonded to the tooth 1 using adhesive or the like. And, the archwire 12 is dropped down into the archwire slot 16 of the orthodontic attachment 11.

Next, the orthodontic cap 13 is pressed against the orthodontic attachment 11 from above to thereby mount the former onto the latter. In this case, the engaging portion receiving portions 22 of the orthodontic cap 13 are engaged with their associated engaging portions 17 of the orthodontic attachment 11 respectively. Since the orthodontic cap 13 includes the engaging portion receiving portions 22 respectively in its two end portions, it can be mounted onto the orthodontic attachment 11 in any arbitrary direction, that is, with no restrictions in the vertical direction.

In other words, the engaging portion receiving portions 22 of the orthodontic cap 13 are engaged with the engaging portions 17 of the orthodontic attachment 11 at positions existing in the vertical direction perpendicular to the mesiodistal direction of the archwire 12 arranged parallel to the teeth row.

Thus, the engaging portion receiving portions 22 of the orthodontic cap 13 can be simply engaged with the engaging portions 17 of the orthodontic attachment 11 at positions free from the influence of the archwire 12.

And, the archwire 12 dropped down in the archwire slot 16 is supported within the archwire slot 16 by the archwire support projection 23 of the orthodontic cap 13 without looseness.

Here, in the case that the orthodontic attachment 11 is formed of plastics, a metal insert is provided therein in order to reinforce the archwire slot 16 of the attachment main body 15.

Figure 6:
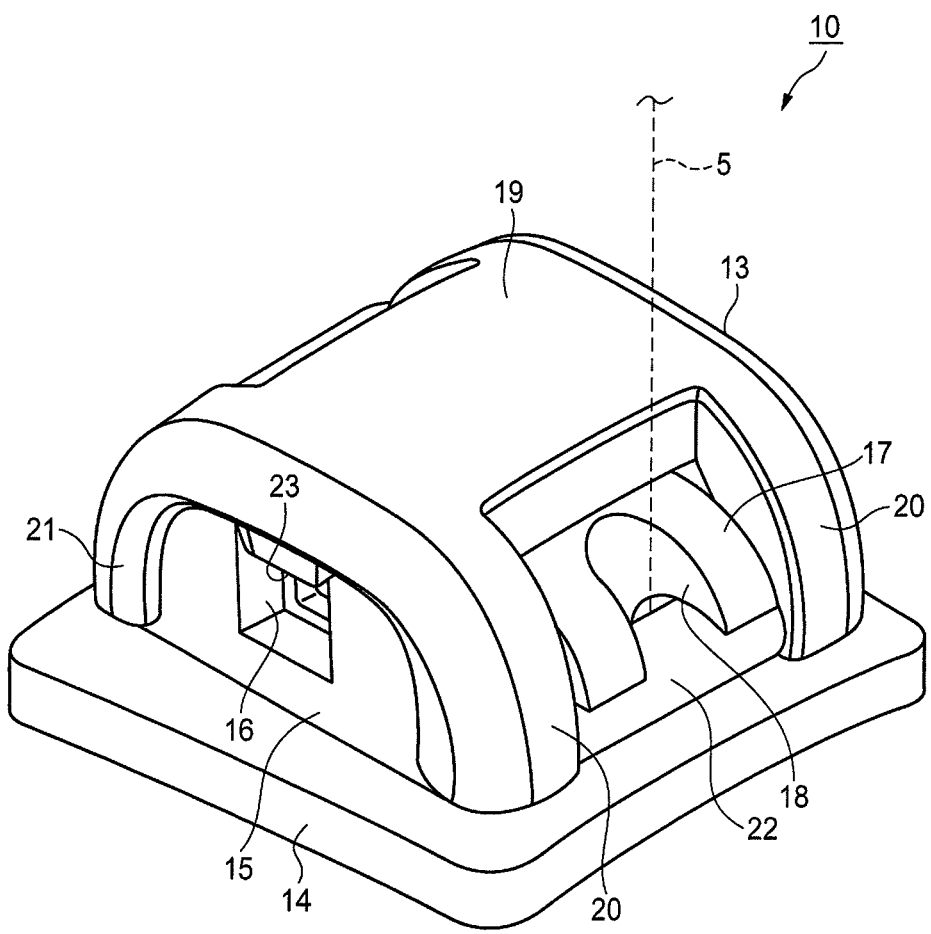
FIG. 6 It is a perspective appearance view of the orthodontic device shown in FIG. 1 when viewed from obliquely upward, explaining how to remove the engagement thereof.

As shown in FIG. 6, when removing the engagement of the orthodontic device 10, a device 5 such as a scaler may be inserted into the cut-out portion 18 of the orthodontic attachment 11 and, while keeping this device 5 in contact with the cap main body 19, the engaging portion receiving portions 22 of the orthodontic cap 13 may be pressed using the principles of the lever.

Consequently, since the engaging portion receiving portions 22 of the orthodontic cap 13 are shifted in the vertical direction perpendicular to the mesiodistal direction, namely, the outward direction of the orthodontic attachment 11, the orthodontic cap 13 can be easily detached from the engaging portions 17 of the orthodontic attachment 11, that is, the engagement thereof can be removed.

Figure 7:
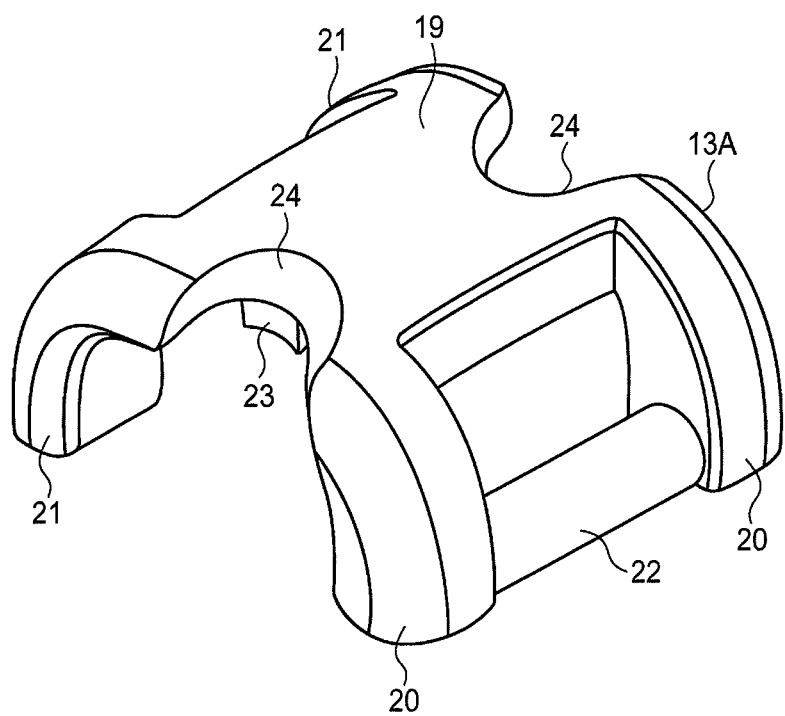
FIG. 7 It is a perspective appearance view of a modification of the orthodontic cap to be applied to the orthodontic device shown in FIG. 1, when viewed from obliquely upward.

FIG. 7 shows a modification of the above-mentioned first embodiment. This orthodontic cap 13A includes a pair of cut-out portions 24 respectively formed in the mesiodistal direction two end portions of the cap main body 19 corresponding to the archwire slot 16. The cut-out portions 24 are used to prevent the orthodontic cap 13A from applying an excessive load to the archwire 12 when the front tooth portion is twisted or when mounting the cap 13A onto the orthodontic attachment 11 mounted on the lingual surface of the tooth. This can reduce frictional resistance between the archwire 12 and archwire slot 16.

In the orthodontic device 10 and the method for mounting and removing the orthodontic cap 13 according to the first embodiment of the invention, when mounting the orthodontic cap 13 onto the orthodontic attachment 11, the orthodontic attachment 11 is bonded to the tooth 1 and the archwire 12 is dropped down into the archwire slot 16 of the orthodontic attachment 11.

Next, while pressing orthodontic cap 13 against the orthodontic attachment 11 from above, the former is mounted onto the latter, and the engaging portion receiving portions 22 of the orthodontic cap 13 are engaged with the engaging portions 17 of the orthodontic cap 13 respectively. In this case, the engaging portion receiving portions 22 of the orthodontic cap 13 are engaged with the engaging portions 17 of the orthodontic cap 13 in a direction perpendicular to the mesiodistal direction of the archwire 12.

Thus, the engaging portion receiving portions 22 of the orthodontic cap 13 can be easily engaged with the engaging the engaging portions 17 of the orthodontic cap 13 at positions free from the influence of the archwire 12. Therefore, when the archwire 12 is retained in the archwire slot 16, the orthodontic device 10 can provide an aesthetic appearance and the orthodontic cap 13 can be easily mounted onto the orthodontic attachment 11.

Also, the archwire 12 dropped down into the archwire slot 16 of the orthodontic attachment 11 is retained by the orthodontic cap 13 through the orthodontic attachment 11. Thus, it is possible to retain the archwire 12 without applying any load directly to the archwire 12. This can reduce frictional resistance between the archwire 12 and archwire slot 16 when the archwire 12 is retained in the archwire slot 16.

Also, when removing the above engagement, a device such as a scaler is inserted into the cut-out portions 18 of the orthodontic attachment 11 to thereby apply pressure against the engaging portion receiving portions 22. As a result, the engaging portion receiving portions 22 are removed from the engaging portions 17 of the orthodontic attachment 11, whereby the engagement of the orthodontic cap 13 is removed. Therefore, the engagement removal can be carried out simply.

Second Embodiment

Next, description will be given below of an orthodontic device and a method for mounting and removing an orthodontic cap according to a second embodiment of the invention. Here, in the following embodiments, the same elements thereof as those of the first embodiment and the elements thereof similar in function to the first embodiment are given the same references and thus the description thereof will be simplified or omitted. Also, an orthodontic attachment is the same in structure as the first embodiment and thus the illustration thereof is omitted.

Figure 8:
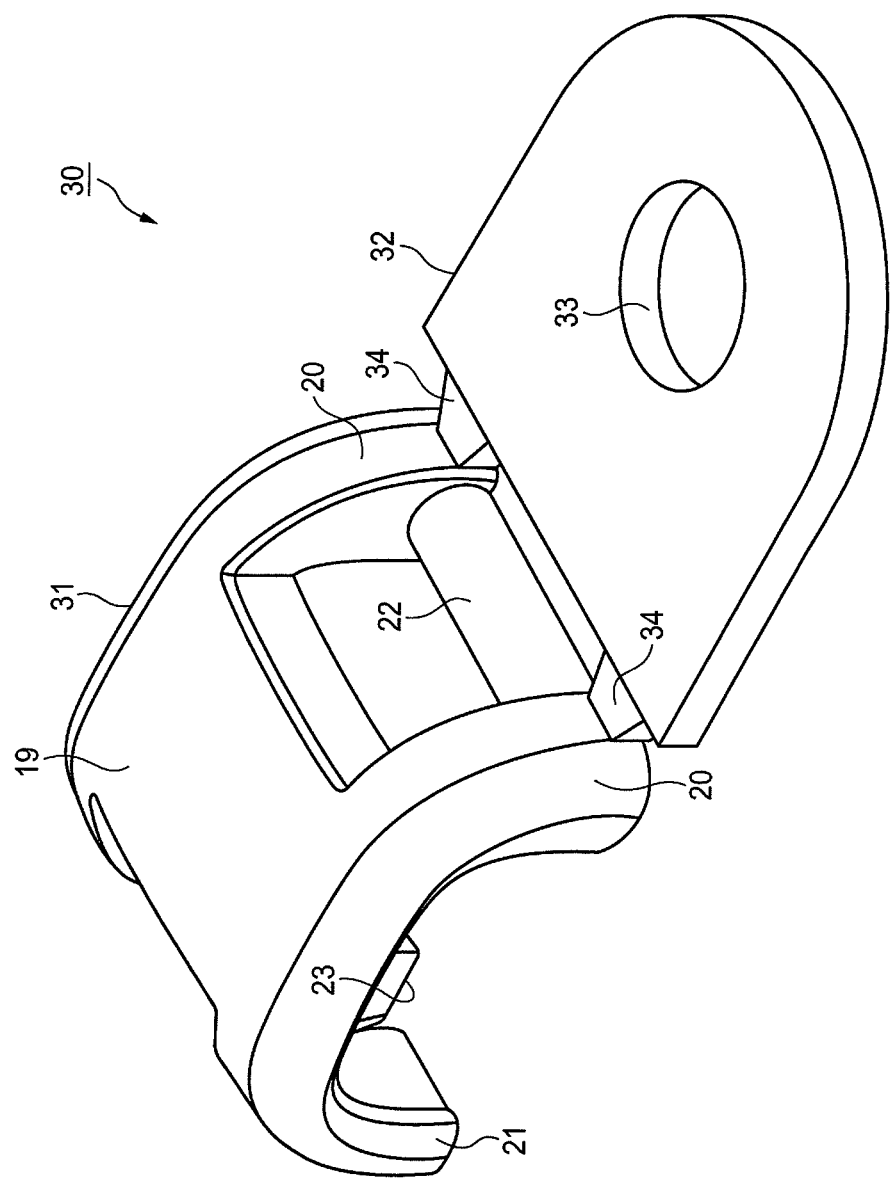
FIG. 8 It is a perspective appearance view of an orthodontic cap to be applied to an orthodontic device according to a second embodiment of the invention, when viewed from obliquely upward.

As shown in FIG. 8, in an orthodontic device 30 according to the second embodiment of the invention, a tab 32 is detachably connected to the foot portions 20 of an orthodontic cap 31. The tab 32 includes a round hole 33.

The tab 32, in order to function as a hold portion when mounting the orthodontic cap 31 onto the orthodontic attachment 11, is formed to have a plate shape which allows easy holding with fingers. The tab 32 is connected to the foot portions 20 through cutting pieces 34. Each cutting piece 34 has an isosceles trapezoids shape in which the tab 32 side thickness thereof is set larger.

In this orthodontic device 30, the archwire 12 is dropped down into the archwire slot 16 of the orthodontic attachment 11 bonded to the tooth 1 and the orthodontic cap 31 is thereafter mounted onto the orthodontic attachment 11. Specifically, after one engaging portion receiving portion 22 situated on the side opposite to the side to which the tab 32 is connected is engaged with one engaging portion 17 of the orthodontic attachment 11, by pulling the tab 32, the orthodontic cap 31 is expanded slightly and the other engaging portion receiving portion 22 on the tab 32 side is engaged with the other engaging portion 17, whereby the orthodontic cap 31 is mounted onto the orthodontic attachment 11.

Next, tweezers or the like is inserted into the round hole 33 of the tab 32 to cut the cutting pieces 34, whereby the tab 32 is wrenched from the orthodontic cap 31.

In the orthodontic device 30 and a method for mounting and removing the orthodontic cap 31 according to the second embodiment of the invention, when mounting the orthodontic cap 31 onto the orthodontic attachment 11 after the orthodontic attachment 11 is bonded to the tooth 1, by holding the tab 32, the handling of the orthodontic cap 31 can be facilitated. Here, the tab 32 may also be connected to the orthodontic cap of the orthodontic device according to other embodiments of the invention.

Third Embodiment

Next, description will be given below of an orthodontic device and a method for mounting and removing an orthodontic cap according to a third embodiment of the invention. Here, the orthodontic attachment thereof is the same in structure to the first embodiment and thus the illustration thereof is omitted here.

Figure 9:
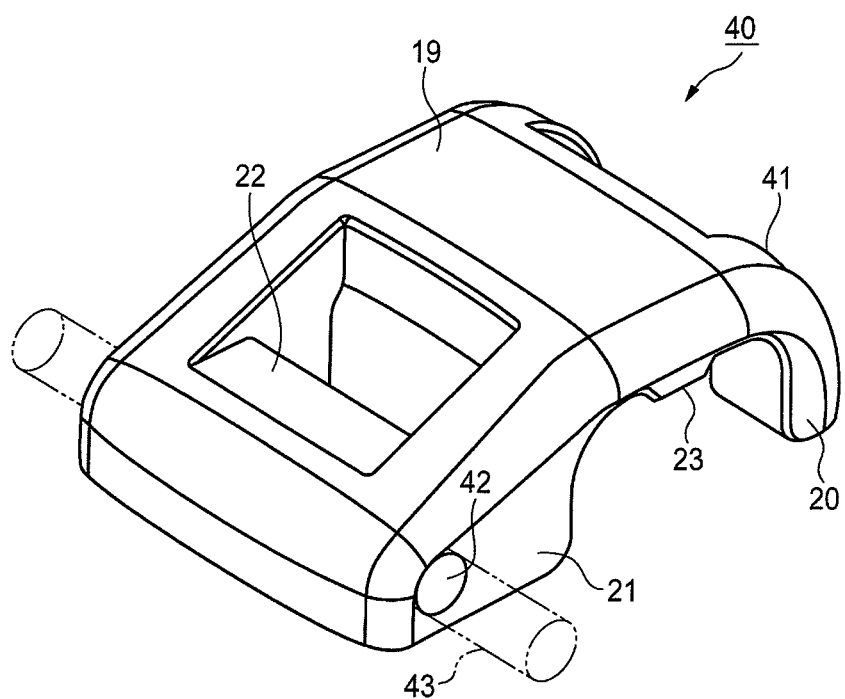
FIG. 9 It is a perspective appearance view of an orthodontic cap to be applied to an orthodontic device according to a third embodiment of the invention, when viewed from obliquely upward.

As shown in FIG. 9, in an orthodontic cap 41 applied to an orthodontic device 40 according to a third embodiment of the invention, there is formed a sub slot 42.

The sub slot 42 is formed as a continuous hole in the foot portion 21 of the orthodontic cap 41 and an auxiliary wire 43 can be inserted into the sub slot 42.

In the orthodontic device 40, the archwire 12 is dropped down into the archwire slot 16 of the orthodontic attachment 11 bonded to the tooth 1 and the orthodontic cap 41 is thereafter mounted onto the orthodontic attachment 11.

Next, an auxiliary wire 43 is inserted into the sub slot 42 of the orthodontic cap 41.

In the orthodontic device 40 and the method for mounting and removing the orthodontic cap 41 according to the third embodiment of the invention, since the sub slot 42 is formed in the orthodontic cap 41, the tooth 1 can be pressed down or pulled up using the auxiliary wire 43 inserted into the sub slot 42.

Fourth Embodiment

Next, description will be given below of an orthodontic device and a method for mounting and removing an orthodontic cap according to a fourth embodiment of the invention. Here, the orthodontic attachment thereof is the same in structure to the first embodiment and thus the illustration thereof is omitted here.

Figure 10:
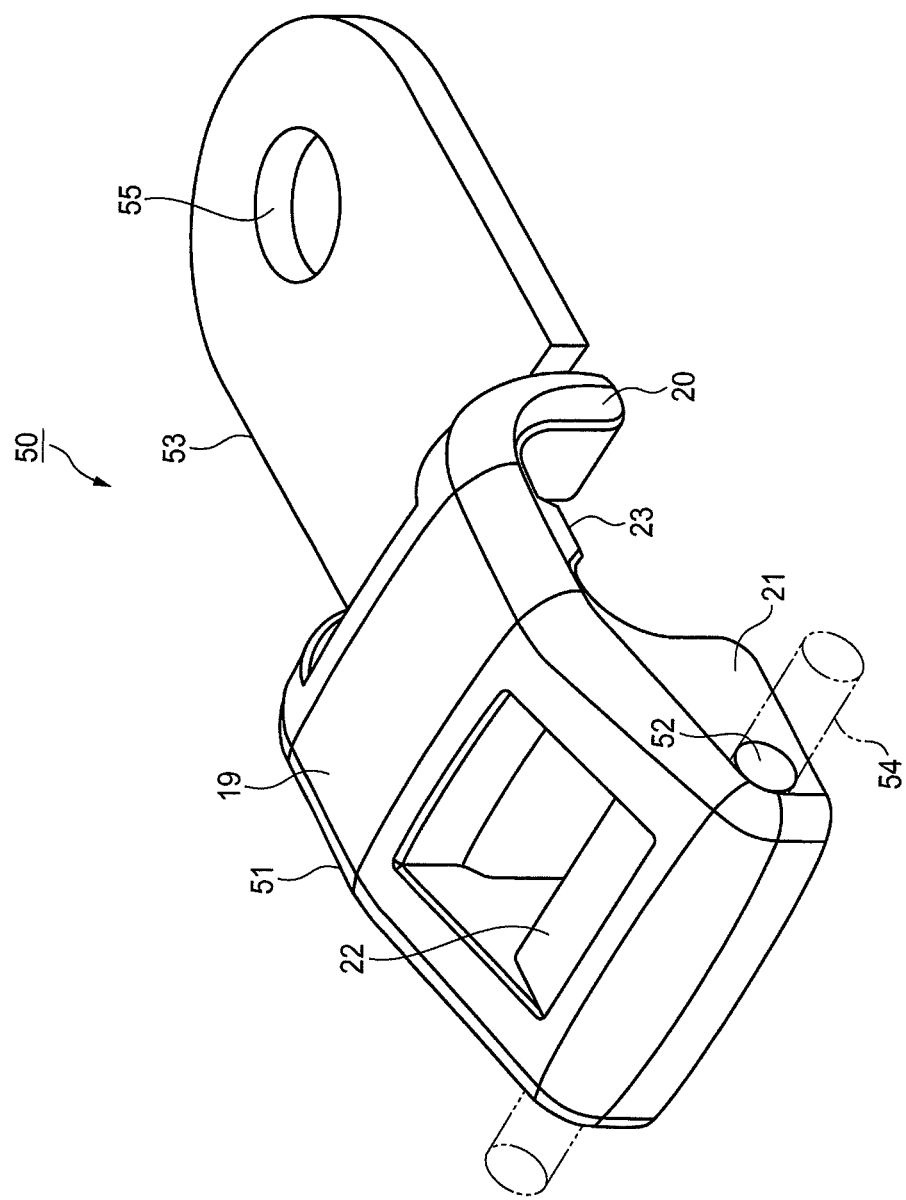
FIG. 10 It is a perspective appearance view of an orthodontic cap to be applied to an orthodontic device according to a fourth embodiment of the invention, when viewed from obliquely upward.

As shown in FIG. 10, in an orthodontic cap 51 applied to an orthodontic device 50 according to the fourth embodiment of the invention, there are formed a sub slot 52 and a tab 53.

The sub slot 52 is formed as a continuous hole in the foot portion 21 of the orthodontic cap 51 and an auxiliary wire 54 can be inserted into the sub slot 52.

The tab 53 is detachably connected to the foot portion 20 and has a round hole 55. The tab 53 is connected to the foot portion 20 through a cutting piece (not shown).

In the orthodontic device 50, the archwire 12 is dropped down into the archwire slot 16 of the orthodontic attachment 11 bonded to the tooth 1 and the orthodontic cap 51 is thereafter mounted onto the orthodontic attachment 11.

Next, a scaler or the like is inserted into the round hole 55 of the tab 53 to cut the cutting pieces, whereby the tab 53 can be wrenched from the orthodontic cap 51. After then, the auxiliary wire 54 is inserted into the sub slot 52 of the orthodontic cap 51.

In the orthodontic device 50 and the method for mounting and removing the orthodontic cap 51 according to the fourth embodiment of the invention, since the sub slot 52 is formed in the orthodontic cap 51, the tooth can be pressed down or pulled up using the auxiliary wire 54 inserted into the sub slot 52.

Also, when mounting the orthodontic cap 51 onto the orthodontic attachment 11, by holding the tab 53, the handling of the orthodontic cap 51 can be facilitated.

Fifth Embodiment

Next, description will be given below of an orthodontic device and a method for mounting and removing an orthodontic cap according to a fifth embodiment of the invention. Here, the orthodontic attachment thereof is the same in structure to the first embodiment and thus the illustration thereof is omitted here.

Figure 11:
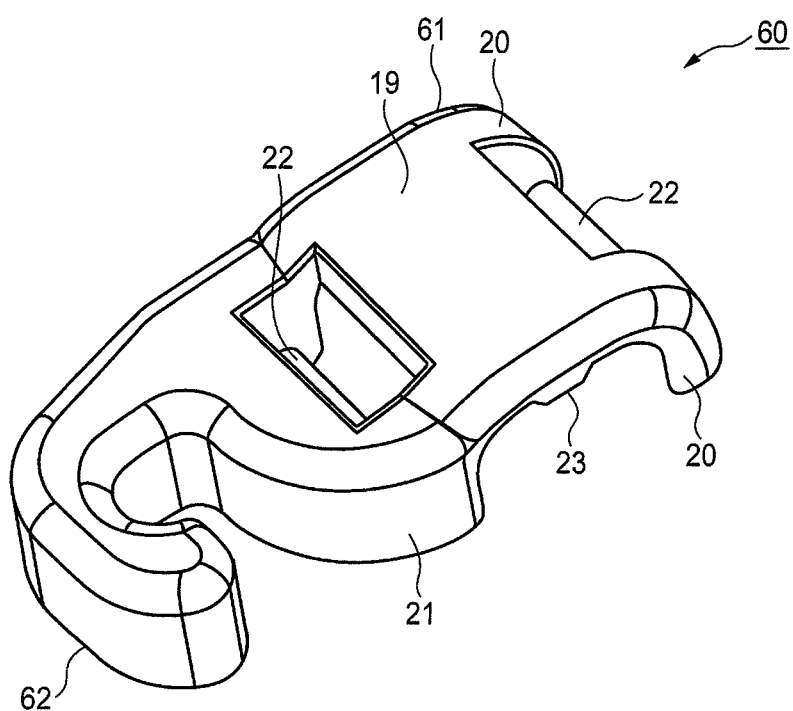
FIG. 11 It is a perspective appearance view of an orthodontic cap to be applied to an orthodontic device according to a fifth embodiment of the invention, when viewed from obliquely upward.

As shown in FIG. 11, in the foot portion 21 of an orthodontic cap 61 applied to an orthodontic device 60 according to the fifth embodiment of the invention, there is formed a power arm 62.

The power arm 62 has a hook-like shape and, in the case that a chain, an elastic member, a coil spring or the like is caught on the power arm 62, the mesiodistal movement of a canine or a premolar can be carried out.

In the orthodontic device 60 and the method for mounting and removing the orthodontic cap 61 according to the fifth embodiment of the invention, since the power arm 62 is formed in the orthodontic cap 61, using a chain, an elastic member, a coil spring or the like caught on the power arm 62, the mesiodistal movement of a canine or a premolar can be carried out.

Sixth Embodiment

Next, description will be given below of an orthodontic device and a method for mounting and removing an orthodontic cap according to a sixth embodiment of the invention. Here, an orthodontic attachment thereof is the same in structure as the first embodiment and thus the illustration thereof is omitted here.

Figure 12:
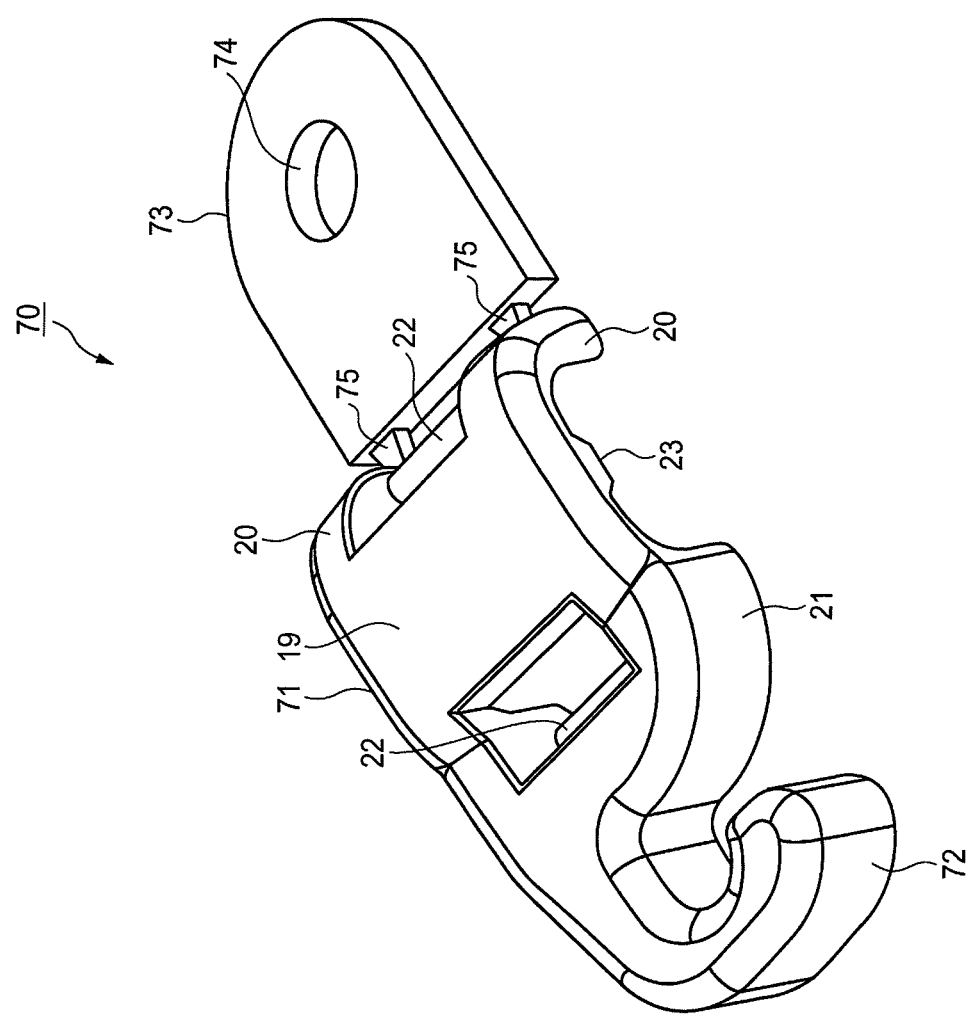
FIG. 12 It is a perspective appearance view of an orthodontic cap to be applied to an orthodontic device according to a sixth embodiment of the invention, when viewed from obliquely upward.

As shown in FIG. 12, an orthodontic cap 71 to be applied to an orthodontic device 70 according to the sixth embodiment of the invention includes a power arm 72 provided on the foot portion 21 thereof, and a tab 73.

The power arm 72 has a hook-like shape and, in the case that a chain, an elastic member, a coil spring or the like is caught thereon, the mesiodistal movement of a canine tooth and a premolar tooth can be carried out.

The tab 73 is detachably connected to the foot portion 20 and has a round hole 74. The tab 73 is connected to the foot portion 20 through cutting pieces 75.

In the orthodontic device 70 and the method for mounting and removing an orthodontic cap 71 according to the sixth embodiment of the invention, due to provision of the power arm 72 on the orthodontic cap 71, in the case that a chain, an elastic member, a coil spring or the like is caught on the power arm 72, the mesiodistal movement of a canine tooth and a bicuspid tooth can be carried out.

Also, when mounting the orthodontic cap 71 onto the orthodontic attachment 11, by holding the tab 73, the handling of the orthodontic cap 71 can be facilitated.

Seventh Embodiment

Next, description will be given below of an orthodontic device and a method for mounting and removing an orthodontic cap according to a seventh embodiment of the invention. Here, an orthodontic attachment thereof is the same in structure as the first embodiment and thus the illustration thereof is omitted here.

Figure 13:
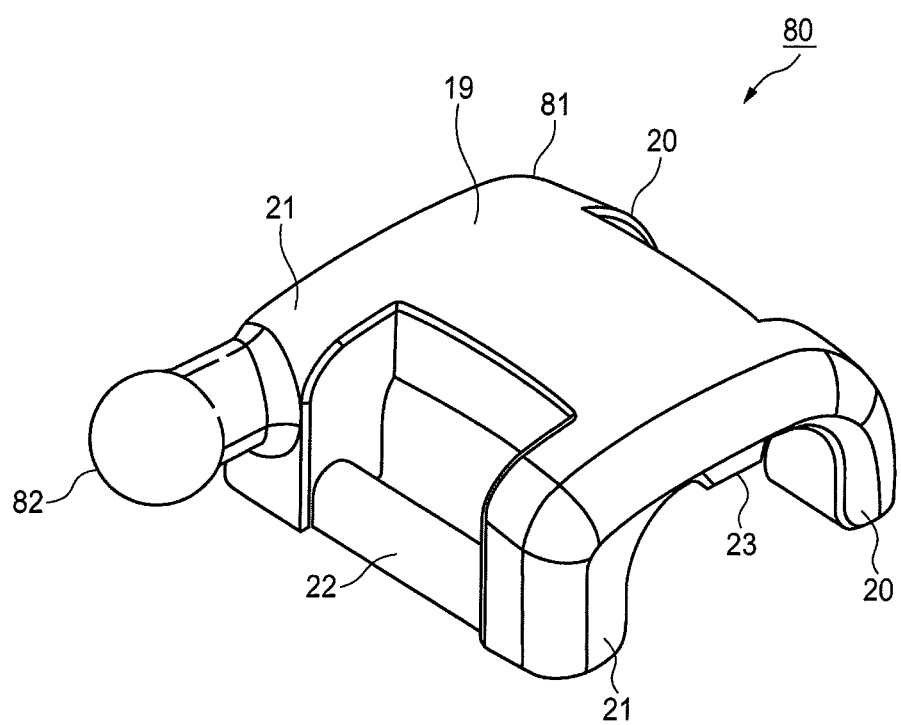
FIG. 13 It is a perspective appearance view of an orthodontic cap to be applied to an orthodontic device according to a seventh embodiment of the invention, when viewed from obliquely upward.

As shown in FIG. 13, an orthodontic cap 81 to be applied to an orthodontic device 80 according to the seventh embodiment of the invention includes a hook 82 provided on the foot portion 21.

The hook 82 has an engaging projection shape and, similarly to the power arm 72, in the case that a chain, an elastic member, a coil spring or the like is caught on the hook 82, the mesiodistal movement of a canine tooth or a premolar can be carried out.

In the orthodontic device 80 and the method for mounting and removing an orthodontic cap 81 according to the seventh embodiment of the invention, due to provision of the hook 82 on the orthodontic cap 81, in the case that a chain, an elastic member, a coil spring or the like is caught on the hook 82, the mesiodistal movement of a canine tooth and a premolar can be carried out.

Eighth Embodiment

Next, description will be given below of an orthodontic device and a method for mounting and removing an orthodontic cap according to an eighth embodiment of the invention. Here, an orthodontic attachment thereof is the same in structure as the first embodiment and thus the illustration thereof is omitted here.

Figure 14:
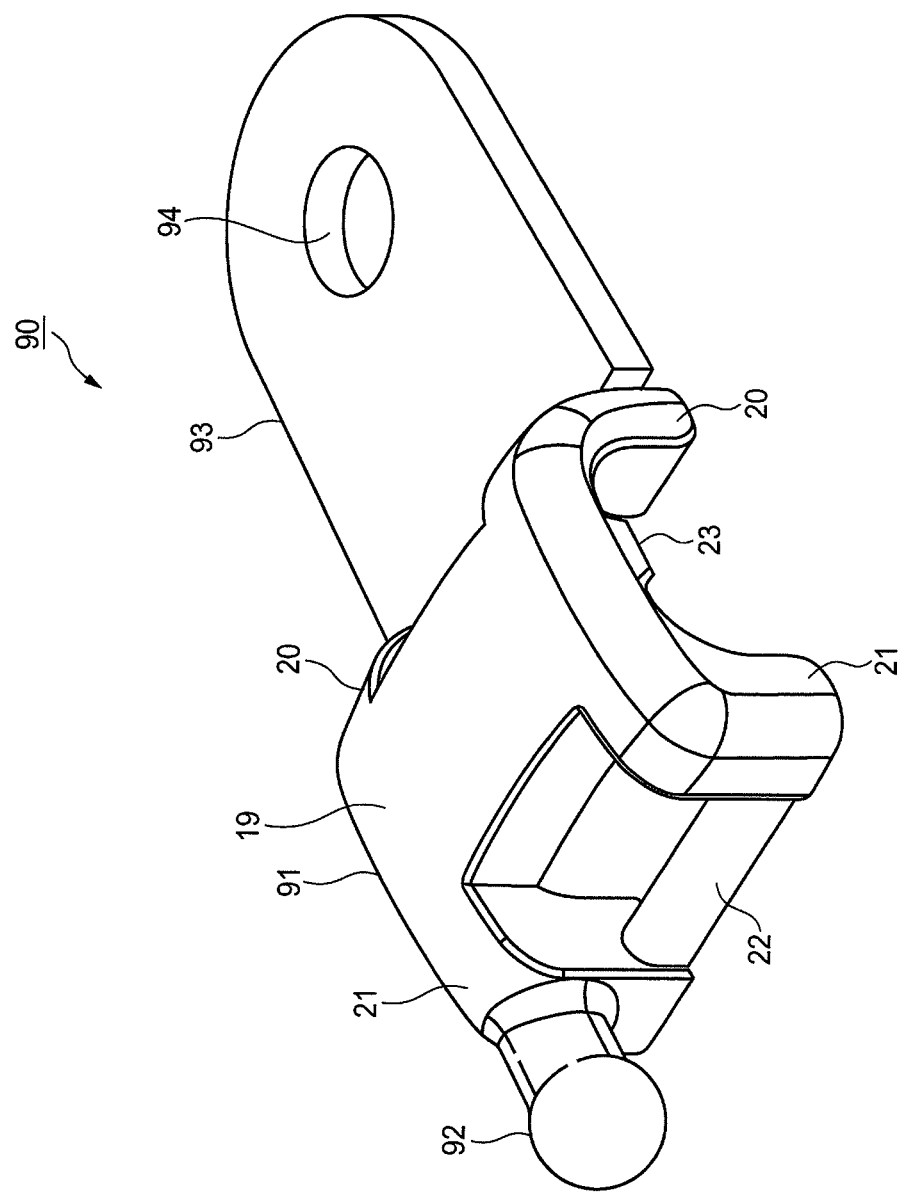
FIG. 14 It is a perspective appearance view of an orthodontic cap to be applied to an orthodontic device according to an eighth embodiment of the invention, when viewed from obliquely upward.

As shown in FIG. 14, an orthodontic cap 91 to be applied to an orthodontic device 90 according to the eighth embodiment of the invention includes a hook 92 provided on the foot portion 21, and a tab 93 having a round hole 94.

In the orthodontic device 90 and the method for mounting and removing an orthodontic cap 91 according to the eighth embodiment of the invention, due to provision of the hook 92 on the orthodontic cap 91, in the case that a chain, an elastic member, a coil spring or the like is caught on the hook 92, the mesiodistal movement of a canine tooth and a premolar can be carried out. Also, when mounting the orthodontic cap 91 onto the orthodontic attachment 11, by holding the tab 93, the handling of the orthodontic cap 91 can be facilitated.

Ninth Embodiment

Next, description will be given below of an orthodontic device and a method for mounting and removing an orthodontic cap according to a ninth embodiment of the invention.

Figure 15:
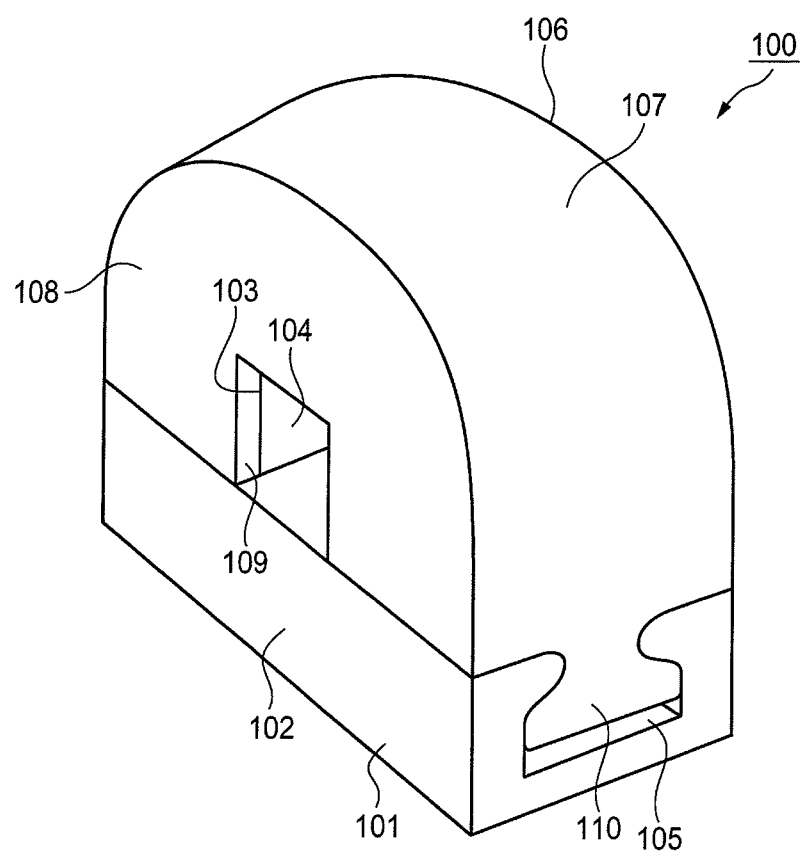
FIG. 15 It is a perspective appearance view of an orthodontic device according to a ninth embodiment of the invention, when viewed from obliquely upward.
Figure 16:
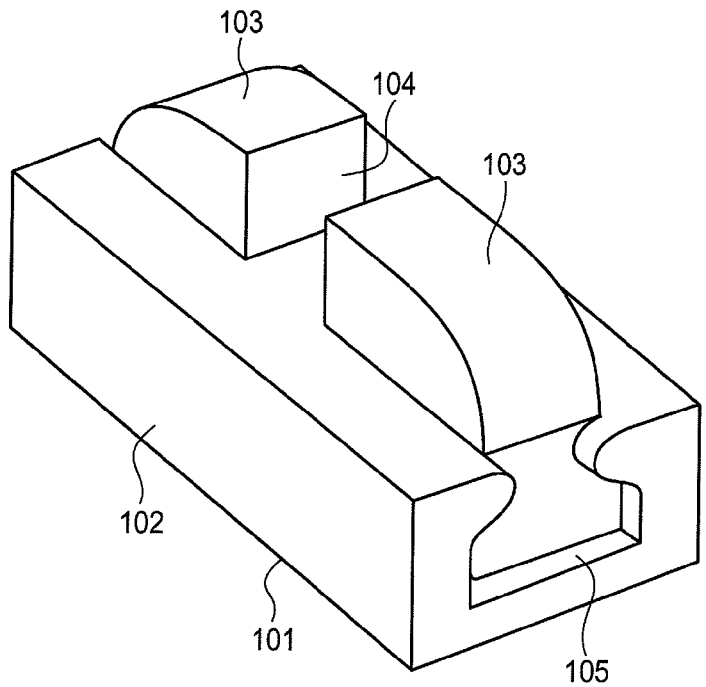
FIG. 16 It is a perspective appearance view of an orthodontic attachment to be applied to the orthodontic device shown in FIG. 15, when viewed from obliquely upward.
Figure 17:
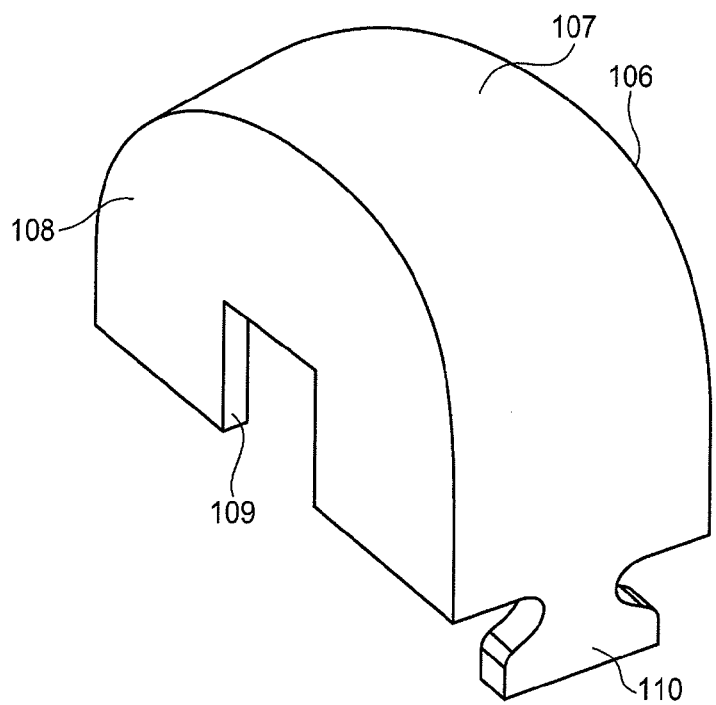
FIG. 17 It is a perspective appearance view of an orthodontic cap to be applied to the orthodontic device shown in FIG. 15, when viewed from obliquely upward.

As shown in FIGS. 15, 16 and 17, in the orthodontic device 100 according to the ninth embodiment of the invention, an orthodontic attachment 101 includes a pair of projecting portions 103 respectively disposed in the central portion of a base 102, an orthodontic attachment side archwire slot 104 interposed between the two projecting portions 103, and two engaging portion receiving portions 105 respectively formed on the two side portions of the base 102.

In the orthodontic device 100 according to the ninth embodiment of the invention, an orthodontic cap 106 includes an arch-shaped top plate 107, a pair of side plates 108 respectively connected to the two side portions of the top plate 107, an orthodontic cap side archwire slot 109 which is formed in the central portion of the side plate 108 and whose lower portion is opened, and two engaging portions 110 respectively formed in the end portions of the top plate 107 and engageable with the engaging portion receiving portions 105 of the orthodontic attachment 101.

In the orthodontic device 100 according to the ninth embodiment, when the orthodontic cap 106 is put on the orthodontic attachment 101, the engaging portions 110 are engaged with their respective engaging portion receiving portions 105. And, the orthodontic attachment side archwire slot 104 and orthodontic cap side archwire slot 109 are integrally and continuously positioned each other.

When removing the engagement of the orthodontic device 100, a device such as a scaler is inserted into the engaging portion receiving portion 105 of the orthodontic attachment 101 and, while keeping the device in contact with the engaging portion receiving portion 105, the engaging portion 110 of the orthodontic cap 106 is pressed using the principles of the lever.

Thus, the engaging portion 110 of the orthodontic cap 106 can be easily removed from the engaging portion receiving portion 105 of the orthodontic attachment 101, whereby the engagement of the orthodontic device 100 can be removed.

The orthodontic device 100 and the method for mounting and removing an orthodontic cap 106 according to the ninth embodiment of the invention can provide similar operation effects to the first embodiment. Especially, in this embodiment, the longitudinal direction width dimension of the archwire 12 can be reduced to thereby be able to obtain a more compact orthodontic device 100.

Tenth Embodiment

Next, description will be given below of an orthodontic device and a method for mounting and removing an orthodontic cap according to a tenth embodiment of the invention.

Figure 18:
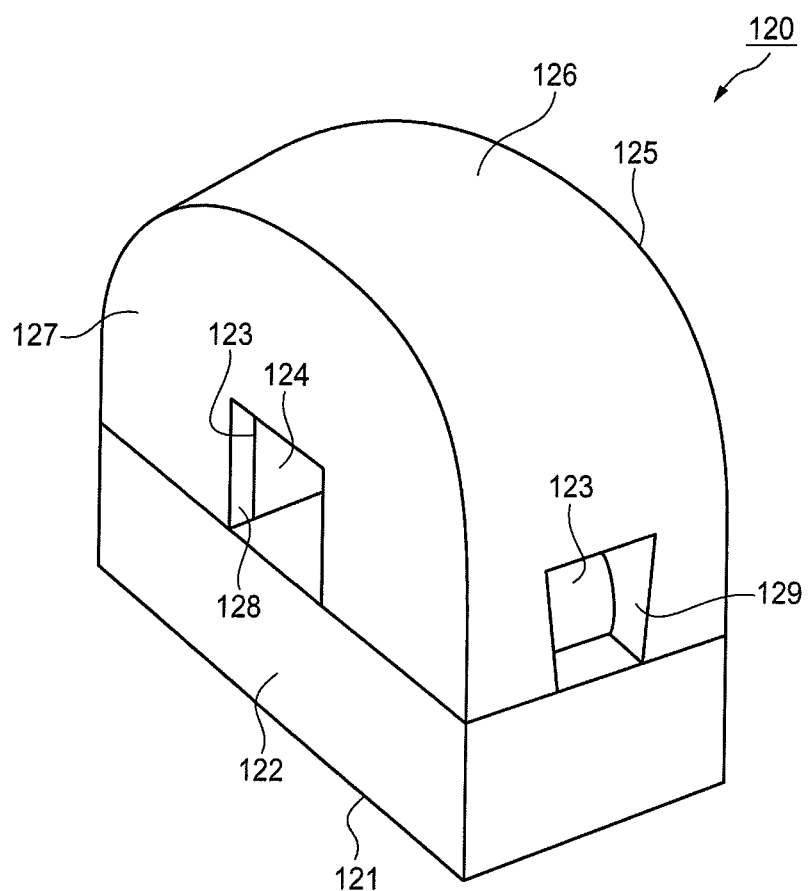
FIG. 18 It is a perspective appearance view of an orthodontic device according to a tenth embodiment of the invention, when viewed from obliquely upward.
Figure 19:
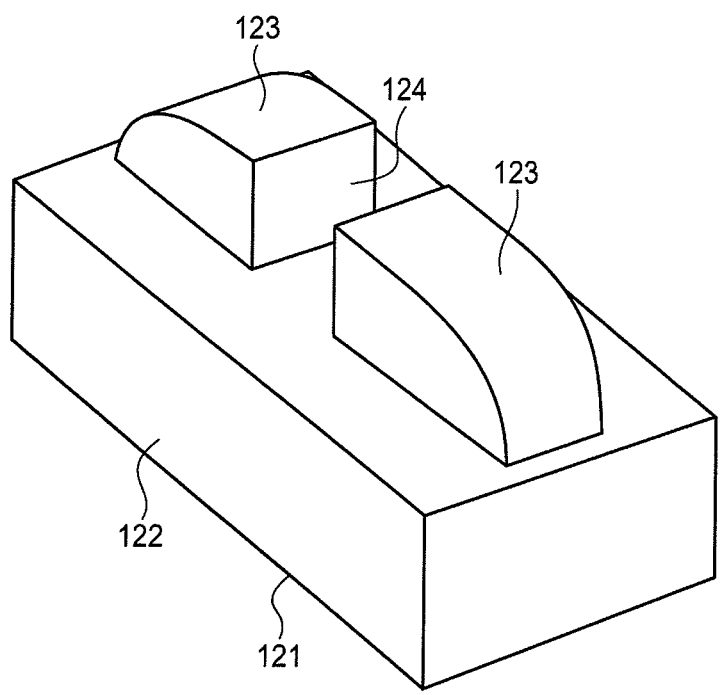
FIG. 19 It is a perspective appearance view of an orthodontic attachment to be applied to the orthodontic device shown in FIG. 18, when viewed from obliquely upward.
Figure 20:
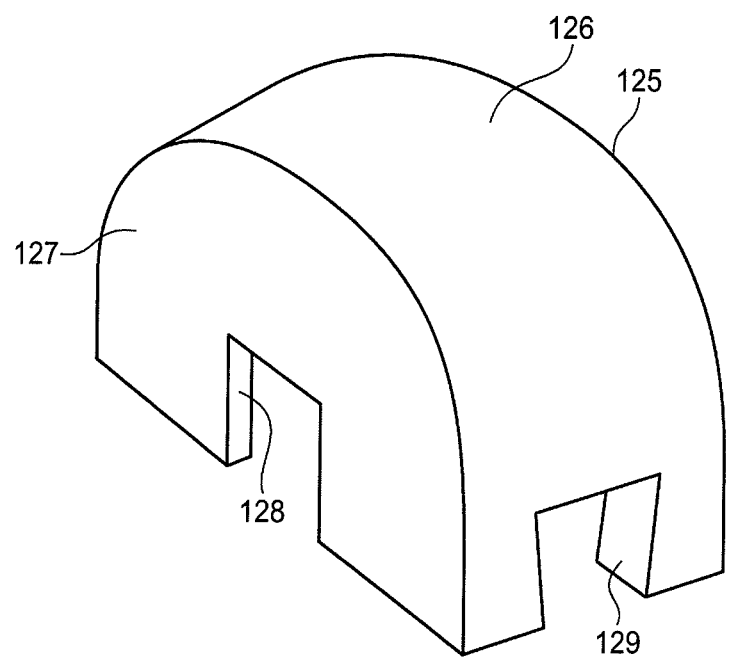
FIG. 20 It is a perspective appearance view of an orthodontic cap to be applied to the orthodontic device shown in FIG. 18, when viewed from obliquely upward.

As shown in FIGS. 18, 19 and 20, in the orthodontic device 120 according to the tenth embodiment of the invention, an orthodontic attachment 121 includes a pair of projecting portions 123 respectively disposed in the central portion of a base 122 and serving also as engaging portions, and an orthodontic attachment side archwire slot 124 interposed between the two projecting portions 123. Here, the width dimension of the base portion (lower end portion) of each projecting portion 123 is set smaller than the width dimension of the upper end portion of the projecting portion 123 along the archwire slot 124.

In the orthodontic device 120 according to the tenth embodiment of the invention, an orthodontic cap 125 includes an arch-shaped top plate 126, a pair of side plates 127 respectively connected to the two side portions of the top plate 126, an orthodontic cap side archwire slot 128 which is formed in the central portion of the side plate 127 and whose lower portion is opened, and two engaging portion receiving portions 129 respectively to be engaged with the projecting portions 123 of the orthodontic attachment 121. Here, each engaging portion receiving portion 129 is formed to have a dovetail groove shape corresponding to the shape of the projecting portion 123.

In the orthodontic device 120 according to the tenth embodiment of the invention, the orthodontic cap 125 is put on the orthodontic attachment 121, whereby the engaging portion receiving portions 129 are engaged with the projecting portions 123 respectively. And, the orthodontic attachment side archwire slot 124 and orthodontic cap side archwire slot 128 are integrally and continuously positioned each other. In this case, since the engaging portion receiving portion 129 is formed to have a dovetail groove shape corresponding to the shape of the projecting portion 123, the engaged state of the projecting portion 123 and engaging portion receiving portion 129 can be secured.

Also, to remove the engagement of the orthodontic device 120, a device such as a scaler may be inserted into the engaging portion receiving portion 129 of the orthodontic cap 125 and, while keeping the device in contact with the projecting portion 123, the engaging portion receiving portion 129 of the orthodontic cap 125 may be pressed using the principles of the lever.

Thus, the engaging portion receiving portion 129 of the orthodontic cap 125 can be removed easily from the projection portion 123 of the orthodontic attachment 121, that is, the engagement of the orthodontic device 120 can be removed.

The orthodontic device 120 and the method for mounting and removing an orthodontic cap 125 according to the tenth embodiment of the invention can provide similar operation effects to the first embodiment. Especially, in this embodiment, the longitudinal direction width dimension of the archwire 12 can be reduced to thereby be able to obtain a more compact orthodontic device 120.

Eleventh Embodiment

Next, description will be given below of an orthodontic device and a method for mounting and removing an orthodontic cap according to an eleventh embodiment of the invention.

Figure 21:
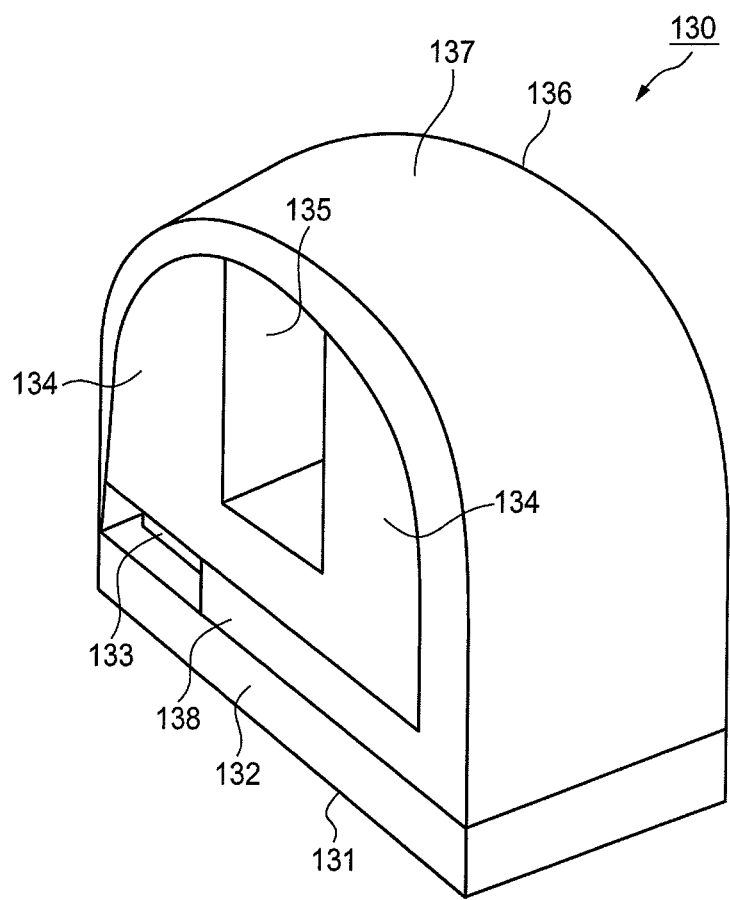
FIG. 21 It is a perspective appearance view of an orthodontic device according to an eleventh embodiment of the invention, when viewed from obliquely upward.
Figure 22:
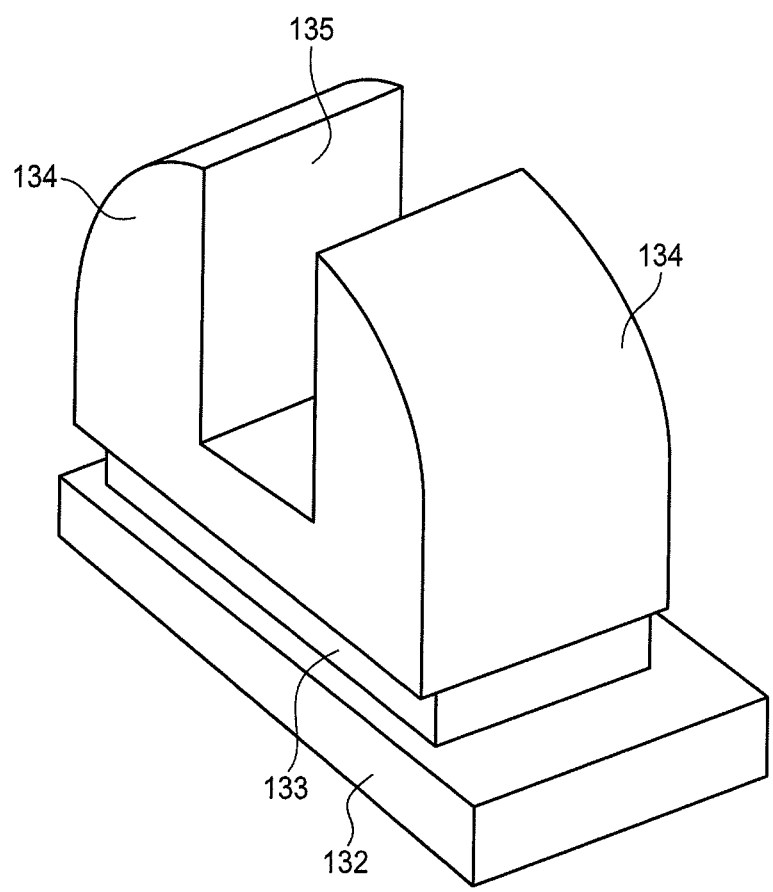
FIG. 22 It is a perspective appearance view of an orthodontic attachment to be applied to the orthodontic device shown in FIG. 21, when viewed from obliquely upward.
Figure 23:
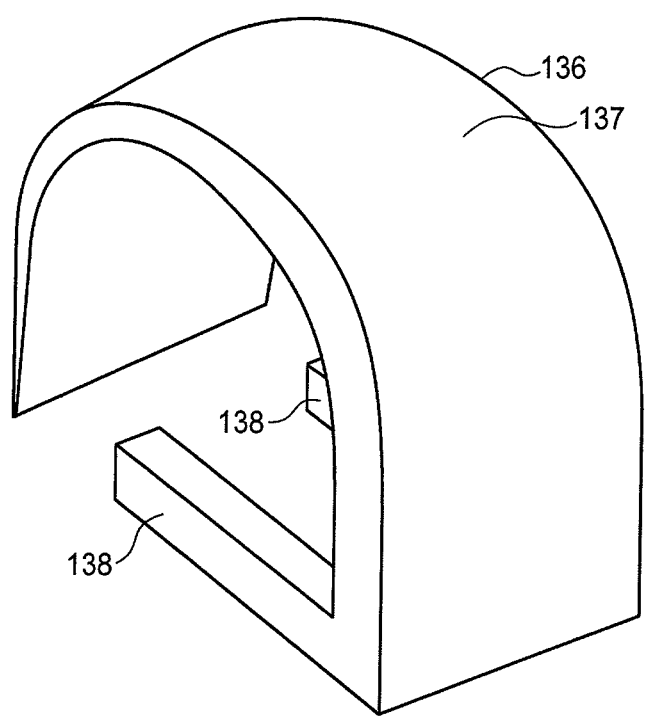
FIG. 23 It is a perspective appearance view of an orthodontic cap to be applied to the orthodontic device shown in FIG. 21, when viewed from obliquely upward.

As shown in FIGS. 21, 22 and 23, in the orthodontic device 130 according to the eleventh embodiment of the invention, an orthodontic attachment 131 includes a pair of projecting portions 134 respectively disposed on the central portion of a base 132 through their associated groove-shaped engaging portion receiving portions 133, and an archwire slot 135 interposed between the two projecting portions 134.

In the orthodontic device 130 according to the eleventh embodiment, an orthodontic cap 136 includes a flexible top plate 137 having an arch-like shape and a pair of engaging portions 138 respectively connected to the bottom portion of the top plate 137.

In the orthodontic device 130 according to the eleventh embodiment, since, while the engaging portions 138 of the orthodontic cap 136 are engaged with the engaging portion receiving portions 133 of the orthodontic attachment 131, the top plate 137 is mounted onto the projecting portions 134, the orthodontic cap 136 can be integrally assembled to the orthodontic attachment 131.

Also, to remove the engagement of the orthodontic device 130, a device such as a scaler may be inserted into the engaging portion receiving portion 133 of the orthodontic attachment 131 and, while keeping the device in contact with the end portion of the engaging portion 138, the engaging portion 138 of the orthodontic cap 136 may be pressed toward the front side in the drawings.

Thus, the engaging portion 138 of the orthodontic cap 136 can be easily removed from the engaging portion receiving portion 133 of the orthodontic attachment 131, that is, while deforming the flexible top plate 137, the engagement of the orthodontic cap 136 can be removed.

The orthodontic device 130 and the method for mounting and removing an orthodontic cap 136 according to the eleventh embodiment of the invention can provide similar operation effects to the first embodiment. Especially, in this embodiment, the orthodontic cap 136 can be easily mounted onto the orthodontic attachment 131.

Twelfth Embodiment

Next, description will be given below of an orthodontic device and a method for mounting and removing an orthodontic cap according to a twelfth embodiment of the invention.

Figure 24:
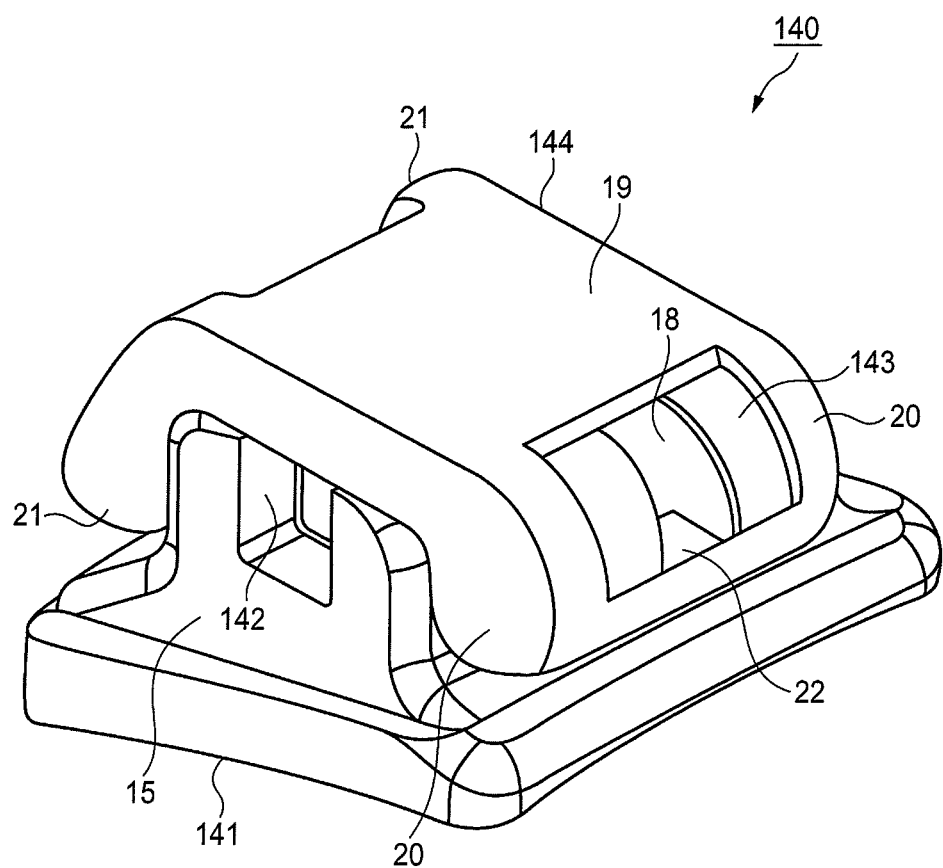
FIG. 24 It is a perspective appearance view of an orthodontic device according to a twelfth embodiment of the invention, when viewed from obliquely upward.
Figure 25:
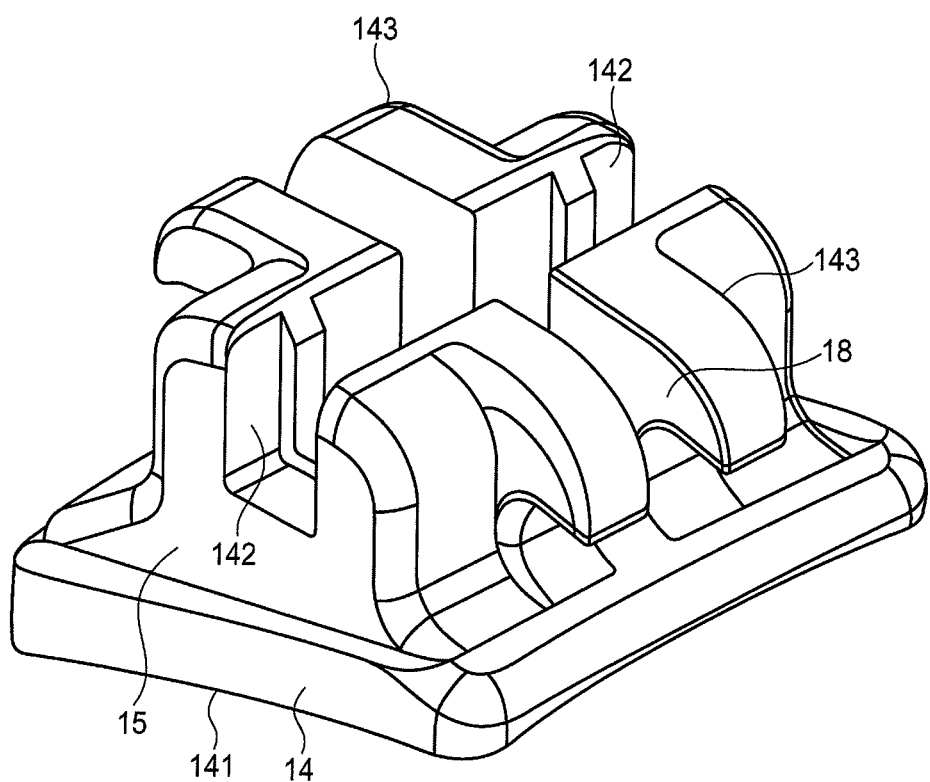
FIG. 25 It is a perspective appearance view of an orthodontic attachment to be applied to the orthodontic device shown in FIG. 24, when viewed from obliquely upward.
Figure 26:
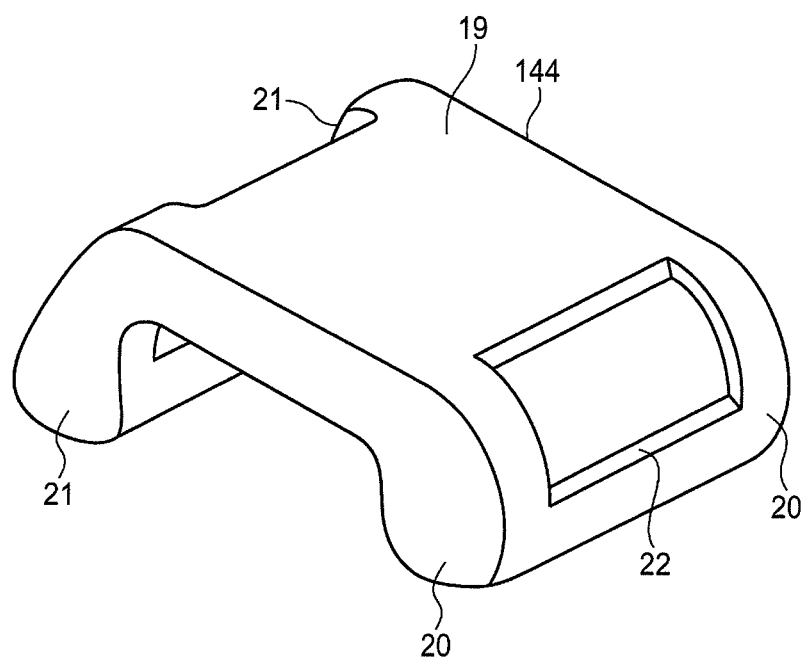
FIG. 26 It is a perspective appearance view of an orthodontic cap to be applied to the orthodontic device shown in FIG. 24, when viewed from obliquely upward.

As shown in FIGS. 24, 25 and 26, in the orthodontic device 140 according to the twelfth embodiment of the invention, an orthodontic attachment 141 includes a pair of engaging portions 143 respectively having a divided archwire slot 142; and, there is used an orthodontic cap 144 similar to the first embodiment.

The orthodontic device 140 and the method for mounting and removing the orthodontic cap 144 according to the twelfth embodiment of the invention can provide similar operation effects to the first embodiment. Especially, in this embodiment, since the engaging portion 143 has the divided archwire slot 142, contact resistance to the archwire 12 can be reduced.

Thirteenth Embodiment

Next, description will be given below of an orthodontic device and a method for mounting and removing an orthodontic cap according to a thirteenth embodiment of the invention.

Figure 27:
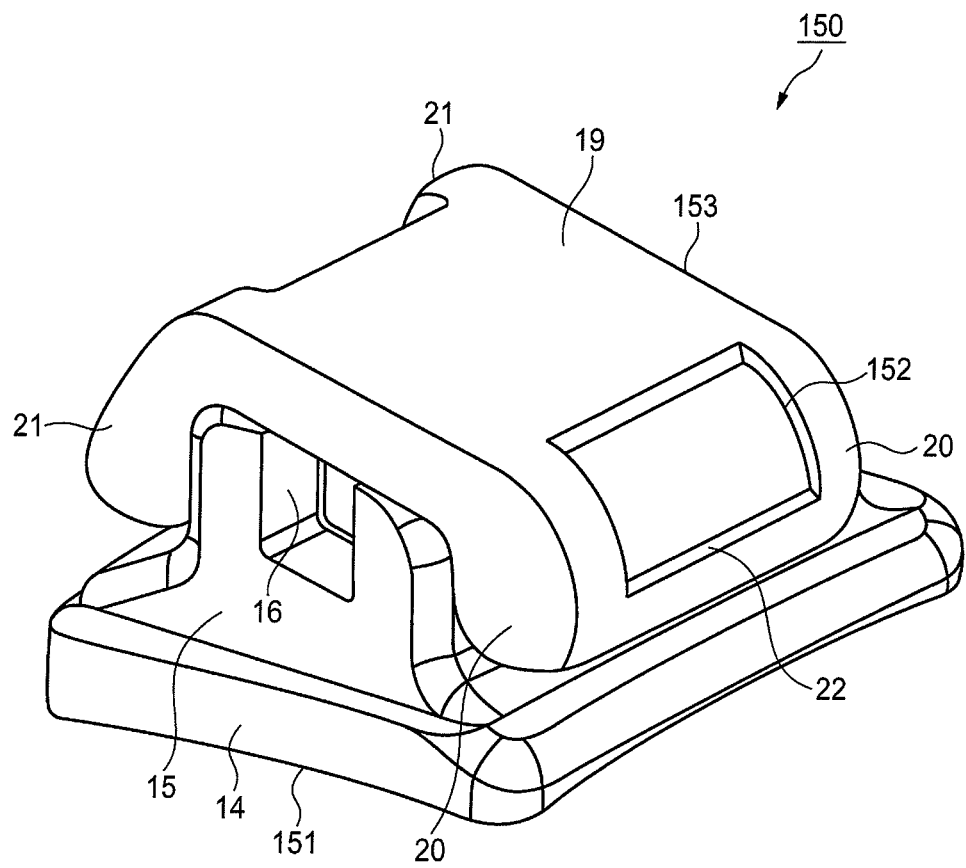
FIG. 27 It is a perspective appearance view of an orthodontic device according to a thirteenth embodiment of the invention, when viewed from obliquely upward.
Figure 28:
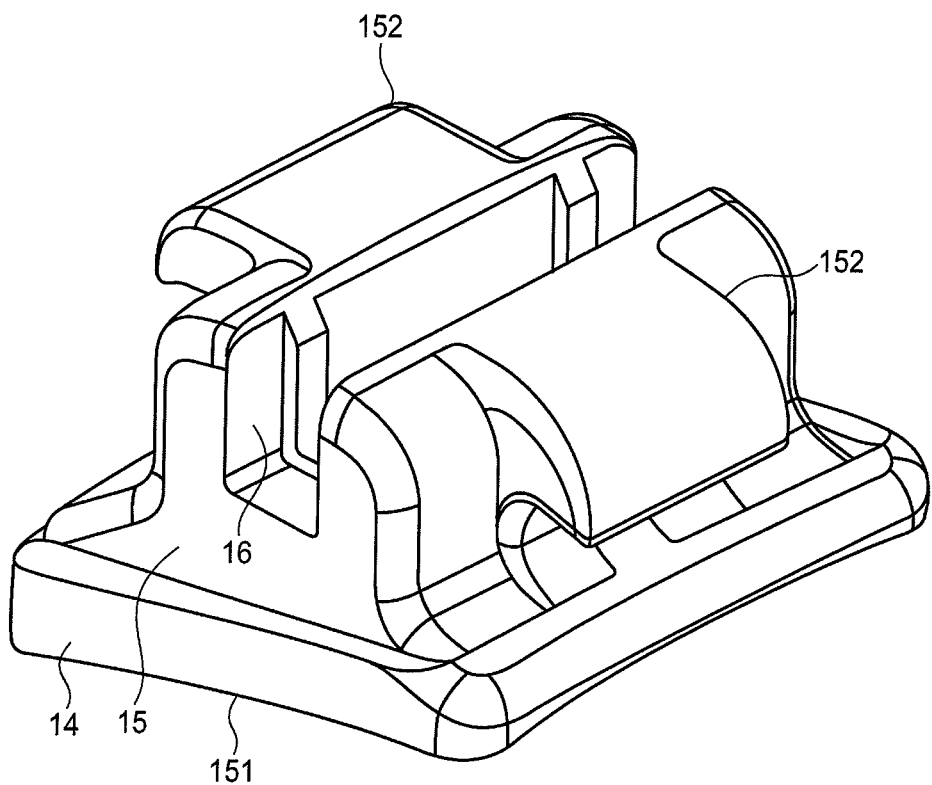
FIG. 28 It is a perspective appearance view of an orthodontic attachment to be applied to the orthodontic device shown in FIG. 27, when viewed from obliquely upward.

As shown in FIGS. 27 and 28, in the orthodontic device 150 according to the thirteenth embodiment of the invention, an orthodontic attachment 151 includes a pair of engaging portions 152; and, there is used an orthodontic cap 153 similar to the first embodiment.

The orthodontic device 150 and the method for mounting and removing the orthodontic cap 153 according to the thirteenth embodiment of the invention can provide similar operation effects to the first embodiment. Especially, in this embodiment, the shape of the apparatus can be simplified further.

Here, the invention is not limited to the above embodiments but modifications, improvements and the like can also be added properly. And, the materials, shapes, dimensions, numeric values, modes, number, locations and the like of the respective elements of the above embodiments are not limitative but are arbitrary, provided that they can attain the invention.

INDUSTRIAL APPLICABILITY

In an orthodontic device and a method for mounting and removing an orthodontic cap according to the invention, in order to correct a teeth row in an orthodontic treatment with an archwire, there are used an orthodontic attachment with an archwire retained thereon and an orthodontic cap to be mounted on the orthodontic attachment. Therefore, the orthodontic device can provide an aesthetic appearance and the orthodontic cap can be easily mounted onto and removed from the orthodontic attachment.

DESCRIPTION OF REFERENCE NUMERALS

10: Orthodontic device
11: Orthodontic attachment
12: Archwire
13: Orthodontic cap
15: Attachment main body
16: Archwire slot
17: Engaging portion
18: Cut-out portion
20, 21: Foot portion
22: Engaging portion receiving portion
23: Archwire support projection
24: Cut-out portion
30: Orthodontic device
31: Orthodontic cap
32: Tab
40: Orthodontic device
41: Orthodontic cap
42: Sub slot
50: Orthodontic device
51: Orthodontic cap
52: Sub slot
53: Tab
60: Orthodontic device
61: Orthodontic cap
62: Power arm
70: Orthodontic device
71: Orthodontic cap
72: Power arm
73: Tab
80: Orthodontic device
81: Orthodontic cap
82: Hook
90: Orthodontic device
91: Orthodontic cap
92: Hook
93: Tab
100: Orthodontic device
101: Orthodontic attachment
103: Projecting portion (engaging portion)
104: Orthodontic attachment side archwire slot
105: Engaging portion receiving portion
106: Orthodontic cap
109: Orthodontic cap side archwire slot
120: Orthodontic device
121: Orthodontic attachment
123: Projecting portion (engaging portion)
124: Orthodontic attachment side archwire slot
125: Orthodontic cap
128: Orthodontic cap side archwire slot
129: Engaging portion receiving portion
130: Orthodontic device
131: Orthodontic attachment
133: Engaging portion receiving portion
135: Archwire slot
136: Orthodontic cap
138: Engaging portion
140: Orthodontic device
141: Orthodontic attachment
142: Archwire slot
143: Engaging portion
144: Orthodontic cap
150: Orthodontic device
151: Orthodontic attachment
152: Engaging portion
153: Orthodontic cap

The invention claimed is:

1. An orthodontic device comprising:
an orthodontic attachment having an archwire slot which stores an archwire therein; and
an orthodontic cap to be mounted on the orthodontic attachment,
wherein the orthodontic attachment includes an engaging portion formed in a side portion of the attachment, and
the orthodontic cap is configured to be mounted on the orthodontic attachment while covering the archwire slot and includes an engaging/receiving portion extending out from a recess portion in a direction perpendicular to an axial direction of the archwire when mounted on the orthodontic attachment and engageable with the engaging portion,
wherein the engaging/receiving portion is interposed between a pair of foot portions on the orthodontic cap,
wherein the engaging portion of the orthodontic attachment includes a cut-out portion for removing the attachment's engagement with the orthodontic cap, and
wherein the cut-out portion being configured to receive a removing device such that when the removing device is inserted into the cut-out portion the engaging/receiving portion of
the orthodontic cap is moved outwardly of the orthodontic attachment and the cap is thereby removed from the engaging portion
wherein the engaging/receiving portion extends a length in the axial direction of tile archwire which is shorter than a length of the archwire slot in the axial direction of the archwire.

2. The orthodontic device as set forth in claim 1, wherein the orthodontic cap includes an archwire support projection extending in a mesiodistal direction of the archwire slot and projecting into the archwire slot when mounted on the orthodontic attachment.

3. The orthodontic device as set forth in claim 1, wherein the orthodontic cap includes a pair of orthodontic cap cut-out recess portions respectively formed in two end portions thereof in the mesiodistal direction of the archwire when mounted on the orthodontic attachment.

4. The orthodontic device as set forth in claim 1, wherein the orthodontic cap includes a sub slot allowing insertion of an auxiliary wire therein.

5. The orthodontic device as set forth in claim 1, wherein the orthodontic cap includes a power arm.

6. The orthodontic device as set forth in claim 1, wherein the orthodontic cap includes a hook.

7. The orthodontic device as set forth in claim 1, wherein the orthodontic cap has axial symmetry with respect to its mesiodistal direction and a tooth axial direction perpendicular to the mesiodistal direction.

8. The orthodontic device as set forth in claim 1, further including a tab detachably connected to the orthodontic cap.

9. The orthodontic device as set forth in claim 1, wherein the orthodontic cap covers the archwire slot completely.

10. The orthodontic device as set forth in claim 1, wherein the engaging/receiving portion is respectively formed to have a cylindrical shape and the pair of foot portions each have a rectangular cross-section.

11. The orthodontic device as set forth in claim 10, wherein the orthodontic cap engages with the attachment by the engaging portion being configured to be inserted in the recessed portion between the engaging/receiving portion and a top surface of the cap.

12. The orthodontic device as set forth in claim 1, wherein the length of the engaging/receiving portion in the axial direction of the archwire is shorter than a length of the orthodonic attachment in the axial direction of the archwire.

* * * * *